United States Patent
Klee et al.

(10) Patent No.: US 9,999,576 B2
(45) Date of Patent: Jun. 19, 2018

(54) DENTAL COMPOSITION

(71) Applicant: DENTSPLY DETREY GMBH, Constance (DE)

(72) Inventors: Joachim E. Klee, Radolfzell (DE); Oliver Elsner, Kussaberg (DE); Sven Pohle, Constance (DE); Helmut Ritter, Wuppertal (DE); Dominika Bernert, Wesel (DE)

(73) Assignee: Dentsply Detrey GMBH, Constance (DE)

( * ) Notice: Subject to any disclaimer, the term of this patent is extended or adjusted under 35 U.S.C. 154(b) by 0 days. days.

(21) Appl. No.: 15/595,017

(22) Filed: May 15, 2017

(65) Prior Publication Data

US 2017/0252271 A1    Sep. 7, 2017

Related U.S. Application Data

(62) Division of application No. 13/504,949, filed as application No. PCT/EP2010/006677 on Nov. 2, 2010, now Pat. No. 9,682,019.

(30) Foreign Application Priority Data

Oct. 30, 2009    (EP) .................................... 09013718

(51) Int. Cl.
  *A61K 6/083*    (2006.01)
  *A61K 6/00*     (2006.01)

(52) U.S. Cl.
  CPC .......... *A61K 6/0835* (2013.01); *A61K 6/0017* (2013.01); *A61K 6/0023* (2013.01); *A61K 6/0038* (2013.01)

(58) Field of Classification Search
  CPC .................................................. A61K 6/0835
  See application file for complete search history.

(56) References Cited

U.S. PATENT DOCUMENTS

| | | | |
|---|---|---|---|
| 3,655,605 A | 4/1972 | Smith et al. | |
| 3,814,717 A | 6/1974 | Wilson et al. | |
| 4,089,830 A | 5/1978 | Tezuka et al. | |
| 4,143,018 A | 3/1979 | Crisp et al. | |
| 4,209,434 A | 6/1980 | Wilson et al. | |
| 4,317,681 A | 3/1982 | Beede et al. | |
| 4,360,605 A | 11/1982 | Schmitt et al. | |
| 4,374,936 A | 2/1983 | Tomioka et al. | |
| 4,376,835 A | 3/1983 | Schmitt et al. | |
| 4,872,936 A | 10/1989 | Engelbrecht | |
| 4,889,948 A | 12/1989 | Mathias et al. | |
| 5,063,257 A | 11/1991 | Akahane et al. | |
| 5,130,347 A | 7/1992 | Mitra | |
| 5,145,374 A | 9/1992 | Stansbury | |
| 5,154,762 A | 10/1992 | Mitra et al. | |
| 5,227,413 A | 7/1993 | Mitra | |
| 5,367,002 A | 11/1994 | Huang et al. | |
| 5,369,142 A | 11/1994 | Culbertson et al. | |
| 5,380,901 A * | 1/1995 | Antonucci | C07F 7/0852 556/440 |
| 5,520,725 A * | 5/1996 | Kato | A61K 6/0023 106/35 |
| 5,859,089 A | 1/1999 | Qian | |
| 5,962,550 A | 10/1999 | Akahane et al. | |
| 5,965,632 A | 10/1999 | Orlowski et al. | |
| 6,124,491 A | 9/2000 | Wolter et al. | |
| 6,177,534 B1 | 1/2001 | Antonucci et al. | |

(Continued)

FOREIGN PATENT DOCUMENTS

| DE | 10058829 A1 | 6/2002 |
|---|---|---|
| DE | 10058830 A1 | 6/2002 |

(Continued)

OTHER PUBLICATIONS

Dong Xie, Jun Zhao and Yiming Weng, Synthesis and Application of Novel Multi-arm Poly(carboxylic acid)s for Glass-ionomer Restoratives, Journal of Biomaterials Applications, Nov. 2008, pp. 1-20.
E. Wasson and J. Nicholson, New Aspects of the Setting of Glass-ionomer Cements, Journal of Dental Research, vol. 72, No. 2, pp. 481-483, Feb. 1993.
Z. Ouyang, S. Sneckberger, E. Kao, B. Culbertson, P. Jagodzinski, New Method for Monitoring the Reaction of Glass-Ionomer Cements: A Spectroscopic Study of the Effects of Polyacid Structure on the Decomposition of Calcium Aluminosilicate Glasses, Applied Spectroscopy, vol. 53, No. 3, pp. 297-301, 1999.
B. Culbertson, D. Xie and A. Thakur, , New Matrix Resins for Glass Polyalkenoates or Glass-Ionomers With Pendant Amino Acid Residues, J.M.S. Pure App. Chem. A 36(5&6), pp. 681-696, 1999.

(Continued)

*Primary Examiner* — Michael F Pepitone
(74) *Attorney, Agent, or Firm* — McNees Wallace & Nurick LLC

(57) ABSTRACT

An aqueous dental glass ionomer composition comprising (a) a reactive particulate glass, (b) a linear or branched polymer comprising acidic groups, which is reactive with the particulate glass in a cement reaction, whereby the linear or branched polymer comprising acidic groups has a polymer backbone and optionally pendant groups, (c) optionally dispersed nanoparticles comprising grafted linear or branched polymer chains comprising acidic groups, and having a polymer backbone characterized in that a polymer backbone of the linear or branched polymer of component (b) and/or, if present, the grafted linear or branched polymer chains of component (c) are obtainable a process comprising (i) cyclopolymerizing or cyclocopolymerizing one or more compounds of the following formula (I):

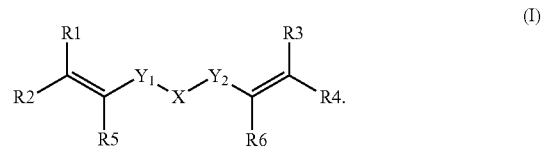

24 Claims, No Drawings

(56) References Cited

U.S. PATENT DOCUMENTS

| | | |
|---|---|---|
| 6,184,339 B1 | 2/2001 | Stansbury et al. |
| 6,447,907 B1 | 9/2002 | Wolter et al. |
| 2004/0254260 A1 | 12/2004 | Mikulla et al. |
| 2005/0261393 A1 | 11/2005 | Mikulla et al. |

FOREIGN PATENT DOCUMENTS

| | | |
|---|---|---|
| EP | 0323120 A2 | 7/1989 |
| EP | 0797975 A2 | 10/1997 |
| WO | 9504026 A1 | 2/1995 |
| WO | 9504109 A1 | 2/1995 |
| WO | 0005182 A1 | 2/2000 |
| WO | 0228912 A2 | 4/2002 |
| WO | 0241845 A1 | 5/2002 |
| WO | 02062861 A1 | 8/2002 |
| WO | 03061606 A1 | 7/2003 |
| WO | 2005117804 A1 | 12/2005 |
| WO | 2006050829 A1 | 5/2006 |

OTHER PUBLICATIONS

M. Marschutz and A. Bernkop-Schnurch, Thiolated polymers: self-crosslinking properties of thiolated 450 kDa poly(acrylic acid) and their influence on mucoadhesion, European Journal of Pharmaceutical Sciences vol. 15, pp. 387-394, 2002.

R. Mathis and J. Ferracane, Properties of a New Glass Ionomer/Composite Resin Hybrid Restorative, Dental Materials/Implantology, Abstract No. 51, p. 113, 1987.

S. Crisp, B. Kent, B. Lewis, A. Ferner and A. Wilson, Glass-ionomer Cement Formulations. II. The Synthesis of Novel Polycarboxylic Acids, Journal of Dental Research vol. 59, No. 6, pp. 1055-1063, Jun. 1980.

H. Prosser and A. Wilson, Litho-ionomer Cements and their Technological Applications, J. Chem. Tech. Biotechnol. vol. 29, pp. 69-87, 1979.

D. Xie, B. Culbertson, G. Wang, Microhardness of N-Vinylpyrrolidone Modified Glass-Ionomer Cements, J.M.S.—Pure Appl. Chem. A 35(4), pp. 547-561 (1998).

* cited by examiner

DENTAL COMPOSITION

CROSS-REFERENCE TO RELATED APPLICATIONS

This application is a divisional application of U.S. patent application Ser. No. 13/504,949, filed Apr. 28, 2012 and issued Jun. 20, 2017 as U.S. Pat. No. 9,682,019, which is a national stage application of PCT Patent Application PCT/EP 2010/006677, filed Nov. 2, 2010, which claims priority from European Patent Application EP20090013718, filed Oct. 30, 2009.

FIELD OF THE INVENTION

The present invention relates to aqueous dental glass ionomer composition comprising a specific polymer comprising acidic groups and optionally additional crosslinkable groups, which has cyclic repeating units in its backbone. Moreover, the present invention relates to a process for the preparation of the specific polymer comprising acidic groups and optionally additional crosslinkable groups, by cyclopolymerization or cyclocopolymerization and optional subsequent further functionalization. Furthermore, the present invention also relates to a process for the preparation of dispersed nanoparticles comprising grafted linear or branched polymer chains comprising acidic groups. Finally, the present invention relates to the use of the specific polymer comprising acidic groups and optionally additional crosslinkable groups, in a cement reaction with a reactive particulate glass. A dental cement hardened by a cement reaction involving the specific polymer comprising acidic groups and optionally additional crosslinkable groups, has reduced shrinkage and improved mechanical properties, in particular with regard to flexural strength and fracture toughness.

BACKGROUND TO THE INVENTION

Conventional glass ionomer cements generally contain a powder component containing aluminosilicate, and a liquid component usually containing an aqueous mixture containing a polymer comprising acidic groups such as polyacrylic acid, polymaleic acid, polyitaconic acid, or a copolymer of at least two of these acids, cf. "New Aspects of the Setting of Glass-ionomer Cements," Wasson et al., Journal of Dental Research; Vol. 72, No. 2, February, 1993; pages 481-483. The most common polymers comprising acidic groups are derived from polyacrylic acid or copolymers of acrylic and itaconic acid (S. Crisp), acrylic acid and maleic acid.

In glass ionomer cements, the primary reactions which cause the glass ionomer cement to harden is crosslinking based on ionic forces between metal ions released from the glass and the polymer comprising acidic groups. Moreover, the acids of the glass ionomer cement partially dilute metal cations from the glass structure during setting so that ionic carboxylates of metal cations may be formed during the setting process.

Glass ionomers used as dental restoratives have advantages over conventional resin containing composites for several reasons. For example, glass ionomers are tolerant to application on wet surfaces, have low shrinkage and are self-adhesive. Since glass ionomers contain polymers rather than monomers, there is no risk of acrylic monomers leaching out, which can lead to sensitization and allergic reactions. Furthermore, glass ionomers bond chemically to dental hard tissues, and may also provide a beneficial level of fluoride release, which helps to prevent recurrent caries. Accordingly, ionomer cements are widely used in the dental field for filling of a cavity, cementing of crowns, inlays, bridges, or orthodontic bands, lining of a cavity, sealing of a root canal, core construction, and preventive sealing.

A key weakness of commercial glass ionomers, however, is their low flexural strength manifesting itself as an undesireable brittleness, which may lead to fracture at the edges of a restoration and, in the worst case, to bulk fracture of a restoration. Therefore, the restorative application of ionomer cements in posterior teeth is usually limited to non-stress bearing areas. Ionomer cement materials continue to have significant limitations for use in permanent posterior restorations, particularly with regard to large restorations.

In order to improve the mechanical properties especially flexural strength and fracture toughness, numerous investigation were carried out, such as the use of amino acid modified polymers (Z. Ouyang, S. K. Sneckberger, E. C. Kao, B. M. Culbertson, P. W. Jagodzinski, Appl. Spectros 53 (1999) 297-301; B. M. Culbertson, D. Xie, A. Thakur, J. Macromol. Sci. Pure Appl. Chem. A 36 (1999) 681-96), application of water soluble copolymers using poly(N-vinylpyrrolidone) (D. Xie, B. M. Culbertson, G. J. Wang, J. Macromol. Sci. Pure Appl. Chem. A 35 (1998) 54761), use of polyacids with narrow molecular weight distribution (DE 100 58 829) and branched polyacids (DE 100 58 830). Further polyacids having a limited molecular mass ranging from 20,000 to 50,000 Da (EP 0 797 975) and 1,000 to 50,000 Da (WO 02/141845) were proposed. A further approach was the application of spherical ionomer particles (WO 00/05182).

Resin-modified glass-ionomer cements were introduced with an aim of overcoming the problems associated with the tendency towards brittle fracture of conventional glass-ionomer, while still retaining advantages such as fluoride release and adhesion (EP 0323120, U.S. Pat. No. 4,872,936 and U.S. Pat. No. 5,154,762). Accordingly, it was suggested to replace some of the water in a conventional glass-ionomer cement with a hydrophilic monomer or to modify the polymeric acid so that some of the acid groups were replaced with polymerisable moieties, so that the polymeric acid could also take part in a polymerisation reaction.

Moreover, in order to address the problem of improving the mechanical properties of ionomer cement materials, U.S. Pat. No. 5,369,142 suggests the use of a specific acidic component, namely copolymers of acryloyl or methacryloyl derivatives of amino acids with acrylic acid or methacrylic acid. WO-A 02/062861 discloses polymer compositions for use in glass ionomer dental restoratives having improved resistance to bending and resistance to twisting, whereby the polymers are formed from at least two specific polymers. WO-A 03/061606 discloses ionomer cements containing amino acids improving the mechanical properties.

Polycondensates or heteropolycondensates based an condensable monomer compounds of silicon were described (U.S. Pat. No. 6,124,491) having a straight or branched organic chain of 4 to 50 carbon atoms and at least one double bond.

Thiolated polymers having self-crosslinking properties and their mucoadhesive properties are disclosed in Marschütz, M. K.; Bernkop-Schnürch A. European Journal of Pharmaceutical Sciences 15 (2002) 387-394.

Synthetic dental compositions formed from cyclopolymerizable bisacrylate and multifunctional oligomer are known from U.S. Pat. No. 5,145,374. Multifunctional acrylates and the synthesis thereof is known from U.S. Pat. No.

5,380,901. These references do not disclose aqueous dental glass ionomer composition comprising

SUMMARY OF THE INVENTION

It is the problem of the present invention to provide novel dental cement systems setting by a cement reaction whereby the cured cement has improved flexural strength and fracture toughness.

This problem is solved according to the invention with an aqueous dental glass ionomer composition comprising
(a) a reactive particulate glass,
(b) a linear or branched polymer comprising acidic groups, which is reactive with the particulate glass in a cement reaction, whereby the linear or branched polymer comprising acidic groups has a polymer backbone and optionally pendant groups,
(c) optionally dispersed nanoparticles comprising grafted linear or branched polymer chains comprising acidic groups, and having a polymer backbone characterized in that a polymer backbone of the linear or branched polymer of component (b) and/or, if present, the grafted linear or branched polymer chains of component (c) are obtainable a process comprising
(i) cyclopolymerizing or cyclocopolymerizing one or more compounds of the following formula (I):

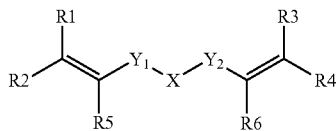

wherein
X is an oxygen atom, a sulfur atom, an $NR^7$ group, or a $CR^8R^9$ group,
$Y^1$ and $Y^2$ which are independent from each other, represent
a $CR^8R^9$ group or a single bond.
$R^1$, $R^2$, $R^3$, $R^4$, $R^5$, $R^6$, $R^7$, $R^8$, and $R^9$ which are independent from each other represent
a hydrogen atom, an alkyl group, a cycloalkyl group, an aryl group, a $ZCOOR^{10}$, ZCN, $ZC(O)NHR^{11}$ and $ZC(O)NR^{12}R^{13}$,
$R^{10}$, $R^{11}$, $R^{12}$ and $R^{13}$ which are independent from each other represents
a hydrogen atom, an alkyl group or an aryl group, and
Z represents a single bond, an alkylene group, a cycloalkylene group or an arylene group,
whereby carboxylic acid groups present in $R^2$ and $R^5$ or $R^4$ and $R^6$ may form a carboxylic acid anhydride moiety, optionally
(ii) reacting a polymer or copolymer obtained by a process comprising step (i) with a compound for introducing one or more functional groups selected from a polymerizable double bond, a thiol group or a carboxylic acid group, and optionally
(iii) repeating step (ii) with a polymer or copolymer obtained by a process comprising step (ii) and (iii).

Furthermore, the present invention provides a process for the preparation of a linear or branched polymer comprising acidic groups, which is reactive with a particulate glass in a cement reaction, whereby the linear or branched polymer comprising acidic groups has a polymer backbone and optionally pendant groups, said process comprising
(i) cyclopolymerizing or cyclocopolymerizing one or more compounds of the following formula (I):

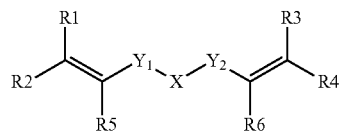

wherein
X is an oxygen atom, a sulfur atom, an $NR^7$ group, or a $CR^8R^9$ group,
$Y^1$ and $Y^2$ which are independent from each other, represent
a $CR^8R^9$ group or a single bond.
$R^1$, $R^2$, $R^3$, $R^4$, $R^5$, $R^6$, $R^7$, $R^8$, and $R^9$ which are independent from each other represent
a hydrogen atom, an alkyl group, a cycloalkyl group, an aryl group, a $ZCOOR^{10}$, ZCN, $ZC(O)NHR^{11}$ and $ZC(O)NR^{12}R^{13}$,
$R^{10}$, $R^{11}$, $R^{12}$ and $R^{13}$ which are independent from each other represents
a hydrogen atom, an alkyl group or an aryl group, and
Z represents a single bond, an alkylene group, a cycloalkylene group or an arylene group,
whereby carboxylic acid groups present in $R^2$ and $R^5$ or $R^4$ and $R^6$ may form a carboxylic acid anhydride moiety, optionally in the presence of one or more compound selected from the group of acrylic acid, methacrylic acid, itaconic acid, itaconic acid anhydride, maleic acid, maleic anhydride, fumaric acid, methyl acrylate, ethyl acrylate, n-butyl acrylate, t-butyl acrylate, 2-ethylhexyl acrylate, methyl methacrylate, ethyl methacrylate, n-butyl methacrylate, t-butyl methacrylate, 2-ethylhexyl methacrylate, cyclohexyl methacrylate, phenyl acrylate, benzyl acrylate, phenyl methacrylate, benzyl methacrylate, 2-phenylethyl methacrylate, 2-hydroxyethyl acrylate, 2-hydroxyethyl methacrylate, hydroxypropyl acrylate, styrene, 8-methylstyrene, vinylpyridine, N-vinylpyrrolidone, vinyl carbazole, vinyldene halide, and acrylonitrile,
optionally
(ii) reacting a polymer or copolymer obtained by a process comprising step (i) with a compound for introducing one or more functional groups selected from a polymerizable double bond, a thiol group or a carboxylic acid group, and optionally
(iii) repeating step (ii) with a polymer or copolymer obtained by a process comprising step (i) and (ii).

Furthermore, the present invention also provides a process for the preparation of dispersed nanoparticles comprising grafted linear or branched polymer chains comprising acidic groups, and having a polymer backbone obtainable as defined by claim 1, said process comprising a step of condensing a mixture containing one or more compounds of the following formulae (II), (III), or (IV) or a hydrolysis product thereof

(II)

(III)

(IV)

wherein

X' represents a hydrolyzable group;

R represents an alkyl, cycloalkyl, cycloalkylalkyl, aralkyl or aryl group,

L, L', L", and L'" which may be the same or different represent independent from each other an organic group, m is an integer $\geq 1$, whereby the sum of X, R, L, L', L", and L'" is 4 for each of formula (II), (III), and (IV), and wherein a portion of L, L', L", and L'" is represented by the following formula:

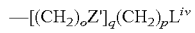

$$-[(CH_2)_oZ']_q(CH_2)_pL^{iv}$$

Z represents an oxygen atom or a sulfur atom, $L^{iv}$ represents a linear or branched polymer moiety comprising acidic groups and having a polymer backbone and optionally pendant groups which is obtainable by a process comprising a step of cyclopolymerizing or cyclocopolymerizing a compound of formula (I) as defined in claim 1, o and p, which are independent from each other, may be the same or different and represent an integer of from 1 to 6, and q represents an integer of from 0 to 12.

Finally, the present invention provides the use of the linear or branched polymer comprising acidic groups, which is reactive with a reactive particulate glass in a cement reaction, whereby the linear or branched polymer comprising acidic groups has a polymer backbone and optionally pendant side chains which is obtainable by a process according to the invention, in a cement reaction with a reactive particulate glass.

DETAILED DESCRIPTION OF THE PREFERRED EMBODIMENTS

According to the invention, an alkyl group may be straight-chain or branched $C_{1-16}$ alkyl group, typically a $C_{1-8}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl. A cycloalkyl group may be a $C_{3-16}$ cycloalkyl group. Examples of the cycloalkyl group can include those having 3 to 14 carbon atoms, for example, cyclopropyl, cyclobutyl, cyclopentyl and cyclohexyl. A cycloalkylalkyl group can include those having 4 to 22 carbon atoms. Examples for a cycloalkylalkyl group can include a combination of a linear or branched alkyl group having 1 to 6 carbon atoms and a cycloalkyl group having 3 to 14 carbon atoms. Examples of the cycloalkylalkyl group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopropyl, propylcyclobutyl, propylcyclopentyl, propylcyclohexyl. An aralkyl group may be a $C_{7-26}$ aralkyl group, typically a combination of a linear or branched alkyl group having 1 to 6 carbon atoms and an aryl group having 6 to 10 carbon atoms. Specific examples of an aralkyl group are a benzyl group or a phenylethyl group. An aryl group can include aryl groups having 6 to 10 carbon atoms. Examples of the aryl group are phenyl and naphtyl.

The $C_{1-6}$ alkyl group and the $C_{3-14}$ cycloalkyl group may optionally be substituted by one or more members of the group selected from a $C_{1-4}$ alkyl group, $C_{1-4}$ alkoxy group, a phenyl group, and a hydroxy group. Examples for a $C_{1-4}$ alkyl group can include linear or branched alkyl groups having 1 to 4 carbon atoms, for example, methyl, ethyl, n-propyl, isopropyl, n-butyl, isobutyl, sec-butyl, tert-butyl. Examples for an $C_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Aryl groups may contain 1 to 3 substituents. Examples of such substituents can include halogen atoms, $C_{1-4}$ alkyl groups, $C_{1-4}$ alkoxy groups, $C_{1-4}$ alkylthio groups, $C_{1-4}$ alkylsulfonyl groups, carboxyl group, $C_{2-5}$ alkoxycarbonyl groups, and $C_{1-4}$ alkylamino groups. Here, illustrative of the halogen atoms can be fluorine, chlorine, bromine and iodine. The $C_{1-4}$ alkyl groups are, for example, methyl, ethyl, n-propyl, isopropyl and n-butyl. Illustrative of the $C_{1-4}$ alkoxy groups are, for example, methoxy, ethoxy and propoxy. Illustrative of the $C_{1-4}$ alkylthio groups are, for example, methylthio, ethylthio and propylthio. Illustrative of the $C_{1-4}$ alkylsulfonyl groups are, for example, methylsulfonyl, ethylsulfonyl and propylsulfonyl, Illustrative of the $C_{2-5}$ alkoxycarbonyl groups can be those having alkoxy groups each of which contains 1 to 4 carbon atoms, for example, methoxycarbonyl, ethoxy carbonyl and propoxycarbonyl. Illustrative of the $C_{1-8}$ alkylamino groups can be those having one or two alkyl groups each of which contains 1 to 4 carbon atoms, for example, methylamino, dimethylamino, ethyl amino and propylamino. The alkyl moieties in these substituents may be linear, branched or cyclic.

The aqueous dental glass ionomer composition according to the invention comprises a reactive particulate glass as a component (a). A particulate reactive glass is a powdered metal oxide or hydroxide, mineral silicate, or ion leachable glass or ceramic, that is capable of reacting with an ionomer in the presence of water to form a hydrogel. The particulate glass may contain mixed oxides of Ca, Ba, Sr, Al, Si, Zn, Na, K, B, Ag, or P. Examples of particulate reactive glass materials include materials commonly known in the art of glass-ionomer cements such as calcium or strontium-containing and aluminum-containing materials. Preferably, particulate reactive fillers contain leachable fluoride ions.

Specific examples of particulate reactive glasses are selected from calcium aluminosilicate glass, calcium aluminumfluorosilicate glass, calcium aluminumfluoroborosilicate glass, strontium aluminosilicate glass, strontium aluminofluorosilicate glass, strontium aluminofluoroborosilicate glass.

Suitable particulate reactive glasses further include metal oxides such as zinc oxide and magnesium oxide, and ion-leachable glasses, e.g., as described in U.S. Pat. No. 3,655,605, U.S. Pat. No. 3,814,717, U.S. Pat. No. 4,143,018, U.S. Pat. No. 4,209,434, U.S. Pat. No. 4,360,605 and U.S. Pat. No. 4,376,835. In a preferred embodiment, the particulate glass is a barium and/or strontium fluoroalumosilicate glass.

According to a preferred embodiment, the reactive particulate glass contains silicon, aluminum, zinc, phosphorus and fluorine as essential elements, whereby silicon, aluminum, zinc and phosphorus are contained in the composition predominantly as oxides.

Specifically, the reactive particulate glass may comprise a. 10-35% by weight of silica
b. 10-35% by weight of alumina
c. 3-30% by weight of zinc oxide
d. 4-30% by weight of P2O5
e. 3-25% by weight of fluoride, Silica (calculated as $SiO_2$) is preferably contained in the glass composition in an amount of from 10-35% by weight. In a more preferred embodiment, silica is contained in an amount of from 20-25% by weight. Alumina (calculated as $Al_2O_3$) is preferably contained in an amount of from 10-35% by weight. In a more preferred embodiment, alumina is contained in an amount of from 20-25% by weight. The weight ratio between silica and alumina is preferably in a range of from 1.2 to 0.8, more preferably in a range of from 1.15 to 1.0.

Zinc oxide (calculated as ZnO) is preferably contained in the glass composition used according to the invention in an amount of from 3-30% by weight. In a more preferred embodiment, zinc oxide is contained in an amount of from 13-18% by weight.

Phosphorus pentoxide (calculated as $P_2O_5$) is preferably contained in the glass composition used according to the invention in an amount of from 4-30% by weight. In a preferred embodiment, phosphorus pentoxide is contained in an amount of from 14 to 18% by weight.

Fluoride is preferably contained in the glass composition according to the invention in an amount of from 3-25% by weight. In a preferred embodiment, fluoride is contained in an amount of from 4-7% by weight.

Besides the preferred essential elements, the particulate glass composition of the present invention may further comprise from 18-21% by weight of calcium oxide plus strontium oxide.

The particulate glass composition preferably essentially does not contain any alkaline metal oxides. In particular, the glass composition contains at most 2% by weight, preferably at most 1.5% by weight, of alkaline metal oxides, $M_2O$, wherein M is Li, Na, or K. In a preferred embodiment, the content of $Na_2O$ in the particulate glass is less than 1% by weight.

The particulate reactive glass may be surface modified by a surface modifying agent. The modifying compound is capable of reacting with surface atoms of the particulate reactive glass, thereby forming a covalent bond between the surface atoms of the particulate reactive glass and the modifying compound.

The surface modifying agent may contain a modifying compound providing a dual function. For example, the modifying compound may contain one or more functional groups capable of taking part in a crosslinking reaction, thereby facilitating the additional crosslinking, whereby the cured cement has improved flexural strength and fracture toughness. The modifying agent may contain one or more modifying compounds.

Preferably, the surface modifying agent contains a hydrolyzable organofunctional silicon compound. The hydrolyzable organofunctional silicon compound may be a compound of one of the following formulae (II), (III) and (IV), or a hydrolysis product thereof

  (II)

  (II)

  (IV)

wherein
X' represents a hydrolyzable group;
R represents an alkyl, cycloalkyl, cycloalkylalkyl, aralkyl or aryl group,
L, L', L", and L'" which may be the same or different represent independent from each other an organic group containing one or more —$S_xH$ groups, wherein x is an integer of from 1 to 6;
m is an integer ≥1,
whereby the sum of X, R, L, L', L", and L'" is 4 for each of formula (II), (III), and (IV).

Preferably, X is a halogen atom or $OR^1$, wherein $R^1$ is an alkyl, cycloalky, cycloalkylalkyl, aralkyl or aryl group. More preferably, R or $R^1$ are independently an alkyl group.

In order to impart crosslinking capability to the organofunctional silicon compound, L, L', L", and L'" may contain —$S_xH$ groups, wherein x is an integer of from 1 to 6, preferably 1, or a polymerizable group, such as a (meth)acrylate group, a (meth)acrylamide group, an allyl group or a vinyl group.

In a preferred embodiment, L, L', L", and L'" may be represented by the following formula:

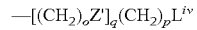

wherein
the Z' which may be the same or different and are independent from each other, represent —NR'—, —O—, S or PR', wherein R' represents independently a hydrogen atom, an alkyl group, a cycloalkyl group, an cycloalkylalkyl group, an aralkyl group or an aryl group,
$L^{iv}$ represents a linear or branched polymer moiety comprising acidic groups and having a polymer backbone and optionally pendant groups with is obtainable by a process comprising a step of cyclopolymerizing or cyclocopolymerizing a compound of formula (I) as defined above, or —$S_xH$, or a polymerizable double bond such as a (meth)acrylate group, a (meth)acrylamide group, an allyl group or a vinyl group,
o and p, which are independent from each other, may be the same or different and represent an integer of from 1 to 6,
q represents an integer of from 0 to 12, and
x is an integer of from 1 to 6.

In a further preferred embodiment, L, L', L", and L'" may be represented by the following formula:

wherein
R', which are independent from each other, may be the same or different and represent a hydrogen atom, an alkyl group, a cycloalkyl group, an cycloalkylalkyl group, an aralkyl group or an aryl group,
$L^{iv}$ represents a linear or branched polymer moiety comprising acidic groups and having a polymer backbone and optionally pendant groups which is obtainable by a process comprising a step of cyclopolymerizing or cyclocopolymerizing a compound of formula (I) as defined above, or —$S_xH$, or a polymerizable double bond such as a (meth)acrylate group, a (meth)acrylamide group, an allyl group or a vinyl group,
o and p, which are independent from each other, may be the same or different and represent an integer of from 1 to 6,
q represents an integer of from 0 to 12 and
x is an integer of from 1 to 6.

In a still further preferred embodiment, L, L', L", and L'" may be represented by the following formula:

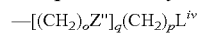

wherein
Z" represents an oxygen atom or a sulfur atom,
$L^{iv}$ represents a linear or branched polymer moiety comprising acidic groups and having a polymer backbone and optionally pendant groups which is obtainable by a process comprising a step of cyclopolymerizing or cyclocopolymerizing a compound of formula (I) as defined above,
o and p, which are independent from each other, may be the same or different and represent an integer of from 1 to 6, and
q represents an integer of from 0 to 12.

Specific examples of modifying compounds contained in the surface modifying agent used in the present invention are 3-mercaptopropyltrimethoxysilane, 3-mercaptopropylmethyldimethoxysilane, 3-mercaptopropyldimethylmethoxysilane, 3-mercaptopropyltriethoxysilane, 3-mercaptopropylmethyldiethoxysilane, 3-mercaptopropyldimethylethoxysilane. The compounds may be used alone or in combination of two or more different compounds.

Based on the treatment of the particulate reactive glass with the surface active agent, the surface of the reactive filler may display functional groups such as L groups which may be used for additional curing reactions such as Michael additions of —$S_xH$ groups to alpha, beta unsaturated ester groups, oxidative coupling reactions of —$S_xH$ groups, en-type reactions, condensation reactions or radical polymerizations.

The surface modifying agent may be used as such or dissolved or dispersed in a suitable solvent. Examples of suitable solvent are toluene, methanol, ethanol, isopropanol, and ethylacetate.

The particulate reactive glass usually has an average particle size of from 0.005 to 100 μm, preferably of from 0.01 to 40 μm as measured using, for example, by electron microscopy or by using a conventional laser diffraction particle sizing method as embodied by a MALVERN Mastersizer S or MALVERN Mastersizer 2000 apparatus. The particulate reactive glass may be a multimodal particulate reactive glass representing a mixture of two or more particulate fractions having different average particle sizes. The particulate reactive glass may also be a mixture of particles of different chemical composition. In particular, it is possible to use a mixture of a particulate reactive material and a particulate non-reactive material.

The aqueous dental glass ionomer composition according to the invention preferably comprises 20 to 80 percent by weight, more preferably 40 to 70 percent by weight, of the reactive particulate glass, based on the weight of the entire composition.

The aqueous dental glass ionomer composition according to the invention further comprises a linear or branched polymer comprising acidic groups as a component (b), which is reactive with the particulate glass in a cement reaction, whereby the linear or branched polymer comprising acidic groups has a polymer backbone and optionally pendant groups. The backbone may comprise acidic groups and/or the pendant groups may comprise acidic groups. The acidic groups are preferably carboxylic acid groups.

Furthermore, the aqueous dental glass ionomer composition according to the invention may optionally further comprise as a component (c) dispersed nanoparticles comprising grafted linear or branched polymer chains comprising acidic groups, and having a polymer backbone.

A polymer backbone of the linear or branched polymer of component (b) and/for, if present, the grafted linear or branched polymer chains of component (c) is obtainable by cyclopolymerizing or cyclocopolymerizing a compound of the following formula (I):

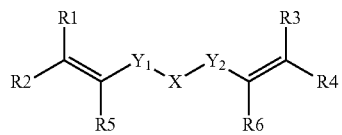

wherein
X is an oxygen atom, a sulfur atom, an $NR^7$ group, or a $CR^8R^9$ group,
$Y^1$ and $Y^2$ which are independent from each other, represent
a $CR^8R^9$ group or a single bond.
$R^1$, $R^2$, $R^3$, $R^4$, $R^5$, $R^6$, $R^7$, $R^8$, and $R^9$ which are independent from each other represent
a hydrogen atom, an alkyl group, a cycloalkyl group, an aryl group, a $ZCOOR^{10}$, ZCN, $ZC(O)NHR^{11}$ and $ZC(O)NR^{12}R^{13}$,
$R^{10}$, $R^{11}$, $R^{12}$ and $R^{13}$ which are independent from each other represents a hydrogen atom, an alkyl group or an aryl group, and
Z represents a single bond, an alkylene group, a cycloalkylene group or an arylene group,
whereby carboxylic acid groups present in $R^2$ and $R^5$ or $R^4$ and $R^6$ may form a carboxylic acid anhydride moiety.

According to formula (I), X is an oxygen atom, a sulfur atom, an $NR^7$ group, or a $CR^8R^9$ group. Preferably, X is an oxygen atom, a $NR^7$ group, or a $CR^8R^9$ group, wherein $R^7$, $R^8$, and $R^9$ which are independent from each other represent preferably a hydrogen atom, an alkyl group, a cycloalkyl group, an aryl group, a $ZCOOR^{10}$, ZCN, $ZC(O)NHR^{11}$ and $ZC(O)NR^{12}R^{13}$, and $R^{10}$, $R^{11}$, $R^{12}$ and $R^{13}$ which are independent from each other represents a hydrogen atom, an alkyl group or an aryl group, and Z is a bond or a $C_{1-6}$ alkylene group.

According to a preferred embodiment, X is an oxygen atom or a $CR^8R^9$ group, wherein $R^8$ and $R^9$ are selected from a hydrogen atom, a $ZCOOR^{10}$, ZCN, $ZC(O)NHR^{11}$ and $ZC(O)NR^{12}R^{13}$ and $R^{10}$, $R^{11}$, $R^{12}$, $R^{13}$ and Z are as defined in claim 1.

According to a further preferred embodiment $R^1$, $R^2$, $R^3$, $R^4$, which are independent from each other represent a hydrogen atom, $ZCOOR^{10}$, $ZC(O)NHR^{11}$ or $ZC(O)NR^{12}R^{13}$, wherein $R^{10}$, $R^{11}$, $R^{12}$ and $R^{13}$ which are independent from each other represents a hydrogen atom, or an alkyl group and Z is a single bond or a $C_{1-3}$ alkylene group. Preferably, at least one of $R^1$, $R^2$, $R^3$, and $R^4$ represents $ZCOOR^{10}$, wherein $R^{10}$ is a hydrogen atom and Z is a single bond or a $C_{1-3}$ alkylene group. According to a specific embodiment $R^1$, $R^2$, $R^3$, and $R^4$ are hydrogen atoms.

According to a further preferred embodiment, $R^5$ and $R^6$, which are independent from each other represent $ZCOOR^{10}$, ZCN, $ZC(O)NHR^{11}$ or $ZC(O)NR^{12}R^{13}$, and $R^{10}$, $R^1$, $R^{12}$, $R^{13}$ and Z are as defined in claim 1. More preferably, $R^5$ and $R^6$, which are independent from each other, may represent $ZCOOR^{10}$, and $R^{10}$ and Z are as defined in claim 1.

According to a preferred embodiment $Y^1$ and $Y^2$ which are independent from each other, represent a $CR^8R^9$ group. According to a further preferred embodiment, at least one of $Y^1$ and $Y^2$ which are independent from each other, represents a single bond.

According to a preferred embodiment $R^8$ and Re which are independent from each other represent $ZCOOR^{10}$, $ZC(O)NHR^{11}$ or $ZC(O)NR^{12}R^{13}$, and wherein $R^{10}$, $R^{11}$, $R^{12}$ and $R^{13}$ which are independent from each other represents a hydrogen atom, or an alkyl group and Z represents a single bond or a $C_{1-6}$ alkylene group. Preferably, at least one of $R^5$ and $R^6$ represents $ZCOOR^{10}$, wherein $R^{10}$ is a hydrogen atom and Z is a single bond or a $C_{1-3}$ alkylene group.

By incorporating the specific polymer backbone according to the invention into the ionomer cement, not only the brittleness may be further improved, but also the mechanical strengths and physical properties are improved.

Certain compounds covered by formula (I) are commercially available compounds. Other compounds may be synthesized according to published procedures. In particular, certain compounds of formula (I) may be synthesised according to the methods disclosed in WO95/04026.

The compounds of formula (I) undergo homo- or co-polymerisation. For example, free radical homopolymerisation of a compound of formula (I) takes place in o-xylene with AIBN as initiator. Accordingly, the present invention provides a process for the preparation of a linear or branched polymer comprising acidic groups, which is reactive with a particulate glass in a cement reaction, whereby the linear or branched polymer comprising acidic groups has a polymer backbone and optionally pendant groups, said process comprising a step of cyclopolymerizing or cyclocopolymerizing a compound of the following formula (I):

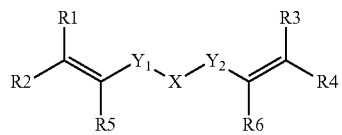

wherein
X is an oxygen atom, a sulfur atom, an $NR^7$ group, or a $CR^8R^9$ group,
$Y^1$ and $Y^2$ which are independent from each other, represent
a $CR^8R^9$ group or a single bond.
$R^1$, $R^2$, $R^3$, $R^4$, $R^5$, $R^6$, $R^7$, $R^8$, and $R^9$ which are independent from each other represent
a hydrogen atom, an alkyl group, a cycloalkyl group, an aryl group, a $ZCOOR^{10}$, ZCN, $ZC(O)NHR^{11}$ and $ZC(O)NR^{12}R^{13}$,
$R^{10}$, $R^{11}$, $R^{12}$ and $R^{13}$ which are independent from each other represents a hydrogen atom, an alkyl group or an aryl group, and
Z represents a single bond, an alkylene group, a cycloalkylene group or an arylene group,
whereby carboxylic acid groups present in $R^2$ and $R^5$ or $R^4$ and $R^6$ may form a carboxylic acid anhydride moiety,
optionally in the presence of one or more polymerizable compounds. When compounds of formula (I) are copolymerised with polymerizable monomers, such monomers may include, for example, polymerizable dicarboxylic acid anhydride monomers, acrylic monomers, styrene monomers, acrylamide monomers.

Preferred comonomers are acrylic acid, methacrylic acid, itaconic acid, itaconic acid anhydride, maleic acid, maleic anhydride, fumaric acid, methyl acrylate, ethyl acrylate, n-butyl acrylate, t-butyl acrylate, 2-ethylhexyl acrylate, methyl methacrylate, ethyl methacrylate, n-butyl methacrylate, t-butyl methacrylate, 2-ethylhexyl methacrylate, cyclohexyl methacrylate, phenyl acrylate, benzyl acrylate, phenyl methacrylate, benzyl methacrylate, 2-phenylethyl methacrylate, 2-hydroxyethyl acrylate, 2-hydroxyethyl methacrylate, hydroxypropyl acrylate, styrene, 8-methylstyrene, vinylpyridine, N-vinylpyrrolidone, vinyl carbazole, vinyldene halide, acrylonitrile, t-butyl acrylate, ethyl methacrylate, n-butyl methacrylate, ethyl triethyleneglycol methacrylate, n-dodecyl acrylate, n-dodecyl methacrylate, 1-tetradecyl methacrylate, 1-hexadecyl acrylate, 1-hexadecyl methacrylate, n-octadecyl acrylate, n-octadecyl methacrylate, tetrahydrofurfuryl acrylate, tetrahydrofurfuryl methacrylate, tetrahydropyranyl methacrylate, phenyl acrylate, benzyl acrylate, 2-cyanoethyl acrylate, 2-hydroxyethyl acrylate, hydroxypropyl acrylate, hydroxypropyl methacrylate, 2,3-dihydroxypropyl acrylate, 2,3-dihydroxypropyl methacrylate, poly(ethylene glycol)(n) monomethacrylate with n=200 and 400, poly(ethylene glycol)(n) monomethyl ether monomethacrylate with n=200; 400 and 1000, 2-isocyanatoethyl acrylate, 2-isocyanatoethyl methacrylate, glycidyl acrylate, glycidyl methacrylate, 2-sulfoethyl methacrylate, 3-sulfopropyl acrylate, 2,2,2-trifluoroethyl acrylate, 2,2,2-trifluoroethyl methacrylate, styrene, a-methylstyrene, 4-cyanostyrene, 4-chlorostyrene, chloromethylstyrene, vinylpyridine, vinyl carbazole, vinylidene halides, acrylonitrile, methacrylonitrile, acrylamide, methacrylamide, N-benzylacrylamide, N-hydroxymethylacrylamide, hydroxymethyldiacetoneacrylamide, N-(2-hydroxypropyl)methacrylamide, vinyl acetate, and N-vinylpyrrolidone.

The polymerizable compounds may preferably be selected from the group of acrylic acid, methacrylic acid, itaconic acid, itaconic acid anhydride, maleic acid, maleic anhydride, fumaric acid, methyl acrylate, ethyl acrylate, n-butyl acrylate, t-butyl acrylate, 2-ethylhexyl acrylate, methyl methacrylate, ethyl methacrylate, n-butyl methacrylate, t-butyl methacrylate, 2-ethylhexyl methacrylate, cyclohexyl methacrylate, phenyl acrylate, benzyl acrylate, phenyl methacrylate, benzyl methacrylate, 2-phenylethyl methacrylate, 2-hydroxyethyl acrylate, 2-hydroxyethyl methacrylate, hydroxypropyl acrylate, styrene, 8-methylstyrene, vinylpyridine, N-vinylpyrrolidone, vinyl carbazole, vinyldene halide, and acrylonitrile.

In a specific embodiment, the comonomer is a polymerizable anhydride such as maleic anhydride or itaconic acid anhydride, which may be hydrolyzed after the formation of the polymer backbone, or which may be further reacted with a compound introducing additional functional groups in a subsequent step. Accordingly, additional acidic groups are available in the polymer backbone which are useful for curing and/or further functionalization.

The process according to the present invention may be carried out by reacting a compound of formula (1) in a suitable solvent in the presence of a radical polymerization initiator for a predetermined time at a predetermined temperature.

Suitable solvents to be used for the process of the present invention may be selected from aromatic or aliphatic hydrocarbons. Examples for suitable solvents include o-xylene, m-xylene, p-xylene, toluene and benzene, whereby o-xylene is preferred. In order for the reaction to proceed, it is preferable to eliminate any oxygen from the solvent prior to the reaction which may be conveniently accomplished by saturating the solvent with an inert gas such as argon or nitrogen.

Suitable radical polymerization initiators include conventional compounds for initiating radical polymerization including organic peroxides such as benzoylperoxide, methylethylketone peroxide, acetone peroxide and tert-butyl hydroperoxide, azo compounds such as N,N-azobisisobutyronitrile and 1,1'azobis(cyclohexanecarbonitrile) peroxides, whereby N,N-azoisobutyronitrile is preferred. The polymerization initiator may be used in a molar ratio of from 0.001:1 to 0.1 to 1 (initiator:monomer)

The reaction temperature is not particularly limited. However, the reaction temperature is preferably in the range of from 25° C. to the boiling temperature of the solvent, more preferably in the range of from 30° C. to 80° C.

The reaction time is not particularly limited. However, the reaction time is preferably in the range of from 30 minutes to 72 hours, preferably in the range of from 1 hour to 48 hours.

The polymer may be recovered by precipitation from the reaction mixture by using a suitable solvent.

It is possible to create a source of additional covalent cross-linking, which imparts additional strength to the ultimate ionomeric cement composition, by reacting a portion of the carboxylic acid groups or carboxylic acid anhydride groups with a further bifunctional monomer containing a carbon-carbon double bond which can take part in an ene-type reaction with the —$S_xH$ groups present in the composition, and/or with a bifunctional monomer containing a reactive alpha,beta-unsaturated moiety which can take part in Michael addition reaction with the —$S_xH$ groups present in the composition, and optionally in a radical polymerization reaction.

Accordingly, the present invention also relates to a linear or branched polymer of component (b) which is obtainable a process comprising cyclopolymerizing or cyclocopolymerizing one or more compounds of formula (I) according to step (i), and subsequently reacting a polymer or copolymer obtained by a process comprising step (i) with a compound for introducing one or more functional groups selected from a polymerizable double bond, a thiol group or a carboxylic acid group, and optionally repeating step (ii) with a polymer or copolymer obtained by a process comprising step (ii) and (iii).

A compound for introducing one or more functional groups selected from a polymerizable double bond, a thiol group or a carboxylic acid group may be a bifunctional compound having a functional group reactive with a carboxylic acid anhydride group, carboxylic acid group, or activated carboxylic acid group whereby an activated carboxylic acid group may be a carboxylic acid chloride, and a further functional group which may be a polymerizable double bond, a thiol group or a carboxylic acid group.

Examples of suitable bifunctional monomers include acryloyl chloride, methacryloyl chloride, vinyl azalactone, allyl isocyanate, 2-hydroxyethylmethacrylate (HEMA), 2-aminoethylmethacrylate, 2-isocyanatoethyl methacrylate (IEM), acrylic acid, methacrylic acid and N-vinylpyrrolidone, cysteamine, allylamine and the like. Other examples of suitable bi-functional monomers are described in U.S. Pat. No. 4,035,321 U.S. Pat. No. 5,130,347.

The linear or branched polymer comprising acidic groups preferably has a molecular weight Mw in the range of from 1,000 to 1000,000, more preferably 5,000 to 400,000.

The aqueous dental glass ionomer composition according to the invention preferably comprises 10 to 80 percent by weight, more preferably 15 to 55 percent by weight, of the linear or branched polymer containing acidic groups, based on the weight of the entire composition.

The aqueous dental glass ionomer composition according to the invention optionally comprises dispersed nanoparticles. The nanoparticles may be nanocondensates obtainable by condensing a mixture containing one or more compounds formula (II), (III), or (IV) as defined above, wherein L, L', L", and L'" may be represented by the following formula:

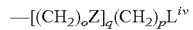
—[(CH$_2$)$_o$Z]$_q$(CH$_2$)$_p$L$^{iv}$

Z represents an oxygen atom or a sulfur atom,

L$^{iv}$ represents a linear or branched polymer moiety comprising acidic groups and having a polymer backbone and optionally pendant groups which is obtainable by a process comprising a step of cyclopolymerizing or cyclocopolymerizing a compound of formula (I) as defined above, o and p, which are independent from each other, may be the same or different and represent an integer of from 1 to 6, and q represents an integer of from 0 to 12.

The condensation of the silane may be carried out by acid catalysis. Suitable acids may be selected from mineral acids such as hydrofluoric acid, hydrochloric acid, phosphoric acid, and sulfuric acid. Condensation may be carried out in the presence of further hydrolysable metal compounds such as metal alkoxides selected from alkoxides of titanium, zirconium, cerium, ytterbium, aluminum, tin, and yttrium. In the absence of co-condensable metal compounds, the particle size distribution is usually narrower than in case of the presence of co-condensable metal compounds. In a preferred embodiment, the dispersed nanoparticles of the aqueous dental glass ionomer composition according to the invention have pendant thiol groups.

The aqueous dental glass ionomer composition according to the invention may comprise from 0 to 75 percent by weight of dispersed nanoparticles based on the weight of the entire composition. Preferably, the composition contains 5 to 50 percent by weight of dispersed nanoparticles based on the weight of the entire composition. In a preferred embodiment, the dispersed nanoparticles have an average particle size of from 1 to 100 nm.

The glass ionomer composition of the present invention may optionally further contain a low molecular compound. The low molecular compound may have a molecular weight Mw in the range of from 100 to 5000, preferably in the range of from 200 to 2000. The low molecular compound may contain one or more —$S_xH$ groups, wherein x is an integer of from 1 to 6. Alternatively, the low molecular compound may contain moieties which may react with the —$S_xH$ groups present in the glass ionomer composition in an ene-type reaction or a Michael addition reaction. Specific examples for suitable polythiol compounds are PEG dithiol (e.g. Aldrich 704369, average molecular weight: 1,500; Aldrich704539 average molecular weight: 3,400), 1,16-Hexadecanedithiol, peptides such as Asn-Arg-Cys-Ser-Gin-Gly-Ser-Cys-Trp-Asn, Reduced=85% (HPLC) C44H67N17O16S2, 1154.24, Trithiocyanuric acid, tetrathiol- and tetrapyrrole-substituted Tetrathiafulvalene derivatives, pentaerythrityl tetrathiol, trimethylolpropane tris(2-mercaptoacetate), trimethylolpropane tris(3-mercaptopropionate), 2,2'-(ethylenedioxy) diethanethiot and pentaerythritol tetrakis(3-mercaptopropionate).

The glass ionomer composition of the present invention may comprise —$S_xH$ groups, wherein x is an integer of from 1 to 6, which crosslink the particulate glass and/or the linear polymer comprising acidic groups and/or the optionally dispersed nanoparticles and/or the low molecular compound. The —$S_xH$ groups, wherein x is an integer of from 1 to 6, are sulfane or polysulfane groups, wherein x is preferably 1 to 3. Specifically, the —$S_xH$ groups are preferably thiol groups (—$S_xH$), disulfane groups (—S—SH) or trisulfane groups (—S—S—SH). In a more preferred embodiment —$S_xH$ groups are thiol groups which may be primary or secondary thiol groups.

When the crosslinking reaction is based on an oxidative coupling of —$S_xH$ groups, the —$S_xH$ groups, wherein x is an integer of from 1 to 6, may be present on any of the reactive particulate glass, the linear or branched polymer containing acidic groups, the optional dispersed nanoparticles, or on the optional low molecular compound present in the composition. Preferably, oxidative coupling is metal catalyzed oxidative coupling in the presence of an oxidizing agent. Accordingly, the composition contains preferably a transition metal ions and an oxidizing agent. Examples of the transition metal ions are iron and manganese ions. Moreover, the composition preferably contains an oxidizing agent. Examples for a suitable oxidizing reagent are peroxides such as hydrogen peroxide or a peroxide compound commonly used as free-radical polymerization initiators.

In a first preferred embodiment, the —$S_xH$ groups are present exclusively on either the reactive particulate glass, the linear or branched polymer containing acidic groups, or the optional dispersed nanoparticles. In case the —$S_xH$ groups are present exclusively on an optional additional low molecular component present in the composition, then it will be necessary that the reactive particulate glass, the linear or branched polymer containing acidic groups, and/or the optional dispersed nanoparticles contain reactive carbon-carbon double bonds which may take part in an ene-type reaction or a Michael addition with the —$S_xH$ groups. Specifically, the —$S_xH$ groups may be present on the linear or branched polymer containing acidic groups.

In a second preferred embodiment, the —$S_xH$ groups are present on at least two members selected from the group of either the reactive particulate glass, the linear or branched polymer containing acidic groups, the optional dispersed nanoparticles, or the optional low molecular compound. Any other member selected from this group may contain reactive carbon-carbon double bonds which may take part in an ene-type reaction or the Michael addition with the —$S_xH$ groups.

In a third preferred embodiment each of the members selected from the group of the reactive particulate glass, the linear or branched polymer containing acidic groups, the optional dispersed nanoparticles, or the optional low molecular compound contains either —$S_xH$ groups or reactive carbon-carbon double bonds which may take part in an ene-type reaction with the —$S_xH$ groups.

Accordingly, in the aqueous dental glass ionomer composition according to the invention, the —$S_xH$ groups may crosslink the particulate glass and/or the linear or branched polymer containing acidic groups and/or the optionally dispersed nanoparticles by oxidative coupling.

In a further preferred embodiment, the sulfane or polysulfane groups of the aqueous dental glass ionomer composition according to the invention crosslink the particulate glass and/or the linear polymer containing acidic groups and/or the optionally dispersed nanoparticles in the absence of oxygen. Preferably, the —$S_xH$ groups in the aqueous dental glass ionomer composition according to the invention crosslink by an —$S_xH$ ene-reaction or a Michael addition.

The dental glass ionomer compositions of the present invention may further contain catalysts for the cross-linking reaction, a retarder, free-radical polymerization initiators, stabilizers, non-reactive fillers, solvents, pigments, nonvitreous fillers, free radical scavengers, polymerization inhibitors, reactive and nonreactive diluents, coupling agents to enhance reactivity of fillers, rheology modifiers, and surfactants (such as to enhance solubility of an inhibitor e. g., polyoxyethylene).

Suitable catalysts for the cross-linking reaction may comprise metal cations, metal complexes and/or metal particles such as metal powder or metal colloids, either alone or in combination with an oxidizing agent such as oxygen, a peroxide and/or an oxidizing metal complex. In one aspect, the catalyst and oxidizing agent may comprise the same material. The metal cations, metal complexes and/or metal particles may comprise iron, nickel, copper, cobalt or platinum atoms, or the corresponding ions thereof. The peroxide may comprise hydrogen peroxide, urea-hydrogen peroxide, ethylmethylketone peroxide, or benzoylperoxide.

Suitable retarders are low molecular weight compounds having multiple carboxylic acid groups such as tartraic acid.

Suitable free-radical polymerization initiators may be selected from organic peroxides such as benzoylperoxide, methylethylketone peroxide, acetone peroxide and tert-butyl hydroperoxide, azo compounds such as azobisisobutyronitrile and 1,1'azobis(cyclohexanecarbonitrile), and halogens such as chlorine, bromine or iodine.

Suitable stabilizers may be selected from reducing agents such as vitamin C, inorganic sulfides and polysulfides and the like.

Suitable non-reactive fillers may be selected from fillers currently used in dental restorative compositions. The filler should be finely divided and preferably has a maximum particle diameter less than about 100 µm and an average particle diameter less than about 10 µm. The filler may have a unimodal or polymodal (e.g., bimodal) particle size distribution. The filler can be an inorganic material. It can also be a crosslinked organic material that is insoluble in the polymerizable resin, and is optionally filled with inorganic filler. The filler can be radiopaque, radiolucent or non-radiopaque.

Examples of suitable non-reactive inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas.

Examples of suitable non-reactive organic filler particles include filled or unfilled pulverized polycarbonates or polyepoxides.

Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

Suitable solvents or nonreactive diluents include alcohols such as ethanol and propanol. Suitable reactive diluents are alpha,beta unsaturated monomers for providing altered properties such as toughness, adhesion, and set time, e.g., 2-hydroxyethyl methacrylate (HEMA), hydroxypropyl methacrylate.

Suitable alpha,beta-unsaturated monomers may be water-soluble, water-miscible or water-dispersible. Water-soluble, water-miscible or water-dispersible acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyoxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-mrethacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-2-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxy-propoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acryalte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

Moreover, a further preferred group of compounds are diallyl compounds such as diallyl amine.

Mixtures of alpha,beta-unsaturated monomers can be added, if desired. Preferably, the mixed but unset cements of the invention will contain a combined weight of about 0.5 to about 40%, more preferably about 1 to about 30%, and most preferably about 5 to 20% water, solvents, diluents and alpha,beta-unsaturated monomers, based on the total weight (including such water, solvents, diluents and alpha,beta-unsaturated monomers) of the mixed but unset cement components.

An example of a suitable free radical scavenger is 4-methoxyphenol.

Suitable polymerization inhibitors may be selected from hydroxytoluene, butylated hydroxytoluene (BHT), hydroquinone, 1,4-benzoquinone, tert-butylpyrocatechol, toluhydroquinone, and 3,4-di-tert-butyl-p-cresol. The amount of inhibitor may be selected from 0.001 to 2% and preferably from 0.02 to 0.5% based on the total weight of the copolymer/comonomer/water mixture.

External energy may alternatively or additionally be employed in order to crosslink the $—S_xH$ groups by oxidative coupling. Sources of external energy may be selected from radiative energy sources such as thermal energy sources, ultrasound energy sources, and/or light energy sources such as ultraviolet lamps or visible lamps. In the event that light energy is employed to crosslink the $—S_xH$ groups by oxidative coupling, the dental glass ionomer composition may additionally comprise photoinitiators and/or photosensitizers such as molecular oxygen, alpha-diketones, orthoquinones, organic dyes, fluorescent dyes or colorants, and/or azo-compounds such as azobisisobutyronitrile and 1,1'azobis(cyclohexanecarbonitrile).

The dental glass ionomer composition may be used in a dental ionomer cement. Two major classes of such cements may be distinguished. The first class relates to conventional glass ionomers employing as their main ingredients a homopolymer or copolymer of an alpha,beta-unsaturated carboxylic acid (e.g., poly acrylic acid, copoly (acrylic, itaconic acid), etc.), a modified particulate reactive filler such as modified fluoroaluminosilicate glass, water, and a chelating agent such as tartaric acid. Such dental ionomer cements may be supplied in powder/liquid formulations that are mixed just before use. The mixture will undergo self-hardening in the dark due to an ionic reaction between the acidic groups of the polycarboxylic acid and cations leached from the glass as well as the crosslinking reaction based on the $—S_xH$ groups. The second major class relates to resin-modified glass ionomer cements. Like a conventional glass ionomer, a resin-modified glass ionomer cement employs a modified particulate reactive filler obtainable according to the process of the present invention, whereby the organic portion of an resin-modified glass ionomer cements is different. In one type of resin-modified glass ionomer cement, the polycarboxylic acid is modified to replace or end-cap some of acidic repeating units with pendent curable groups and a photoinitiator is added to provide a second cure mechanism, e.g., as in U.S. Pat. No. 5,130,347. Acrylate or methacrylate groups may be employed as the pendant curable group. A redox cure system can be added to provide a third cure mechanism, e.g., as in U.S. Pat. No. 5,154,762. In another type of resin-modified glass ionomer cement, the cement includes a polycarboxylic acid, an acrylate or methacrylate-functional monomer and a photoinitiator, e.g., as in Mathis et al., "Properties of a New Glass ionomer/Composite Resin Hybrid Restorative", Abstract No. 51, J. Dent Res., 66:113 (1987) and as in U.S. Pat. No. 5,063,257, U.S. Pat. No. 5,520,725, U.S. Pat. No. 5,859,089 and U.S. Pat. No. 5,962,550. Various monomer-containing or resin-containing cements are also shown in U.S. Pat. No. 4,872,936, U.S. Pat. No. 5,227,413, U.S. Pat. No. 5,367,002 and U.S. Pat. No. 5,965,632. Resin-modified glass ionomer cements may be formulated as powder/liquid or paste/paste systems, and contain water as mixed and applied. They harden in the dark due to the ionic reaction between the acidic groups of the polycarboxylic acid and cations leached from the glass as well as the crosslinking reaction of the particulate glass and/or the linear polycarboxylic acid and/or the optionally dispersed nanoparticles when the pH of the aqueous dental glass ionomer composition is at least 6 at the end of the main setting reaction of the linear polycarboxylic acid reactive with the particulate glass. Moreover, resin-modified glass ionomer cements also cure on exposure of the cement to light from a dental curing lamp.

Methods for preparing the glass ionomer compositions are well known, (Crisp et al., "Glass ionomer cement formulations. II. The synthesis of novel polycarboxylic acids," in J. Dent. Res. 59 (6): 1055-1063 (1980)). A dental ionomer cement is prepared by mixing the ionomer with the particulate reactive filler and optionally nanoparticles in the presence of water. The components of the ionomer cement system can be combined (such as by mixing or blending) in a variety of manners and amounts in order to form the ionomer cements of the present invention. For example, a concentrated aqueous solution of the ionomer may be mixed with the modified particulate reactive filler and optionally further components at the time of use. The resultant combination of ionomer, modified particulate reactive filler and water allows the setting reaction to begin. Alternatively, the ionomer and the modified particulate reactive filler are provided as a freeze-dried or lyophilized powdered blend under conditions in which there is not sufficient water to allow the setting reaction to proceed. Such systems can then be combined with water at the time of use in order to begin the setting reaction. Once the setting reaction has begun, the resultant mixture may be formed into its desired shape, followed by curing and allowing the mixture to fully harden. In general, the weight-to-weight ratio of the ionomer to water is from about 1:10 to about 10:1. In general, the concentration of ionomer in water ranges from 25 to 90% by weight, and preferably from 40 to 65% by weight. The resultant aqueous solution has a ratio of polymer to liquid generally ranging from about 1.5 to 8.

The reaction mixture may also include a retarding or modifying agent such as tartaric acid, for adjusting the working time and a setting time, respectively, when preparing the cement as described in U.S. Pat. No. 4,089,830, U.S. Pat. No. 4,209,434, U.S. Pat. No. 4,317,681 and U.S. Pat. No. 4,374,936. In general, an increase in working time results in an increase in setting time as well. The "working time" is the time between the beginning of the setting reaction when the ionomer and modified particulate reactive filler are combined in the presence of water, and the time the setting reaction proceeds to the point when it is no longer practical to perform further physical work upon the system, e.g. spatulate it or reshape it, for its intended dental or medical application. The "setting time" is the time measured from the beginning of the setting reaction in a restoration to the time sufficient hardening has occurred to allow subsequent clinical or surgical procedures to be performed on the surface of the restoration.

In the setting reaction, the modified particulate reactive glass behaves like a base and reacts with the acidic ionomer to form a metal polysalt which acts as the binding matrix (Prosser, J. Chem. Tech. Biotechnol. 29: 69-87(1979)). Moreover, due to the presence of —$S_xH$ groups, crosslinking of the particulate glass and/or the linear polycarboxylic acid and/or the optionally dispersed nanoparticles when the pH of the aqueous dental glass ionomer composition is at least 6 during the reaction of the linear polycarboxylic acid reactive with the particulate glass takes place. Thereby the bonding within the cement does not only rely on ionic salt bridges which are problematic with regard to the mechanical properties, but also on covalent and complex bonding. The setting reaction is therefore characterized as a dual chemical cure system that proceeds automatically in the presence of water. The cement sets to a gel-like state within a few minutes and rapidly hardens to develop strength. Further reactions are polymerisation reactions and polyaddition reactions.

The dental composition is a multi-pack, preferably a two-pack composition. The composition may be a paste/paste system, a powder/liquid system, or a liquid/paste system. The composition is designed so as to avoid premature curing of the components. For this purpose, the reactive inorganic filler component and any acid group containing component must be formulated so as to avoid a premature cement reaction. In a first embodiment, the reactive inorganic glass is contained in a first pack and any acid group containing component is contained in a second pack. The first pack may be a powder or a paste. The second pack may be a liquid or paste. In a second embodiment, the first pack is a powder comprising the reactive inorganic filler and a solid polyacid such as polyacrylic acid, and the second pack is a paste or liquid and contains a further acid group containing component.

The ratio of powder to liquid affects the workability of the mixed ionomer cement systems. Weight ratios higher than 20:1 tend to exhibit poor workability, while ratios below 1:1 tend to exhibit poor mechanical properties, e. g., strength, and hence are not preferred. Preferred ratios are on the order of about 1:3 to about 6:1 and preferably about 1:1 to 4:1.

The invention will now be further illustrated by the following Examples. All percentages refer to percentages by weight unless stated otherwise.

EXAMPLES

Preparative Example 1

Synthesis of polytetrahydropyran-3,5-dicarboxylic acid

1. Synthesis of 2-hydroxymethacrylic acid ethylester

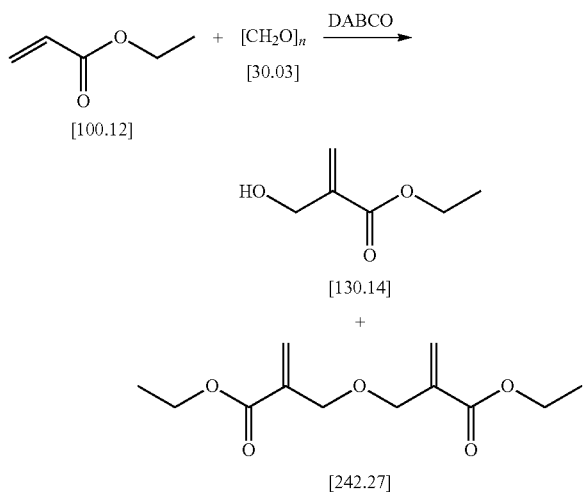

In a 100 ml flask, 10.0 g (0.1 mol) acrylic acid ethyl ester, 2.2 g (0.072 mol) paraformaldehyde and 0.80 g (7.2 mmol) 1,4-diazabicyclo[2.2.2]octane are introduced and stirred over a period of several days a root temperature. The originally turbid reaction mixture turns eventually clear. The raw product is purified by flash chromatography (ethyl acetate/hexane, 1:1). The fractions are combined, hydrochinone is added and the solvent is removed under vacuum. A clear liquid is obtained.

Fraction 2 to 7:

IR: 2982, 2936, 2910, 2872 (ν, —CH$_3$, —CH$_2$), 1710 (ν, —COOR), 1637 (ν, —C=C), 1460, 1447, 1375 (δ, —CH$_3$, —CH$_2$), 1156, 1093 (ν, —C—O—C—), 948 (ν, RCH=CH$_2$) cm$^{-1}$.

$^1$H-NMR (500 MHz, CDCl$_3$): δ 6.31, 5.89 (δ, 4H, RC—CH=CH$_2$), 4.25 (s, 4H, RC—CH$_2$—O—CH$_2$—CR), 4.22 (q, 4H, RCO—CH$_2$—CH$_3$), 1.30 (t, 6H, RC—CH$_3$) ppm.

GC/MS: m/z 197 (C10H13O4+), 169 (C9H13O3+), 129 (C6H9O3+), 113 (C6H9O2+), 73 (C3H5O2+), 69 (C4H5O+), 57 (C3H5O+), 55 (C3H3O+), 45 (C2H5O+).

Fraction 9 to 13:

IR: 3415 (vvv, —OH), 2983, 2939, 2907, 2872 (ν, —CH$_3$, —CH$_2$), 1706 (ν, —COOR), 1636 (ν, —C=C), 1463, 1448, 1387 (δ, —CH$_3$, —CH$_2$), 1152, 1051 (ν, —C—O—), 947 (ν, RCH=CH$_2$) cm$^{-1}$.

$^1$H-NMR (500 MHz, CDCl$_3$): δ 6.25, 5.82 (s, 2H, RC—CH=CH$_2$), 4.33 (s, 2H, RC—CH$_2$—OH), 4.25 (q, 2H, RCO—CH$_2$—CH$_3$), 2.28 (s, 1H, —OH), 1.32 (t, 3H, RC—CH$_3$) ppm.

GC/MS: m/z 129 (M–H+), 113 (C6H9O2+), 101 (C4H5O3+), 85 (C4H5O2+), 73 (C3H5O2+), 57 (C3H5O+), 45 (C2H5O+).

2. Synthesis of polydiethyltetrahydropyrane-3,5-dicarboxylate

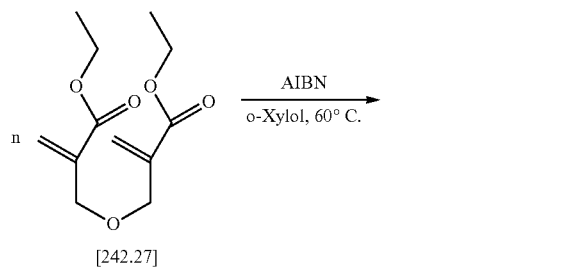

[242.27]

In a 100 mL two-neck flask, equipped with a magnetic stirrer and gas inlet, 10.0 g o-xylene and 1.0 g (4.13 mmol) oxybis-methacrylat are introduced and the mixture is saturated with argon gas for 30 minutes. Subsequently, 6.78 mg (0.041 mmol) N,N-azoisobutyronitrile is added and the reaction mixture is heated to 60° C. Stirring is continued for 24 hours under an argon atmosphere. The polymer solution is precipitated with n-hexane and dried in order to obtain a white powder.

IR: 2981, 2933, 2904, 2869 (ν, —CH$_3$, —CH$_2$), 1724 (ν, —COOR), 1638 (ν, —C=C), 1467, 1445, 1384 (δ, —CH$_3$, —CH$_2$), 1154, 1098, 860 (ν, —C—O—C—) cm$^{-1}$.

$^1$H-NMR (500 MHz, CDCl$_3$): δ 4.21 (br q, 2H, RCOOCH$_2$CH$_3$), 4.10, 3.78 (br dd, 2H, RCH$_2$OCH$_2$R), 2.83 (br d, 2H, RO$_2$CCCH$_2$CCO$_2$R), 1.63 (br s, R—CH$_2$—Cyclo), 1.30 (br t, RCOOCH$_2$CH$_3$) ppm.

GPC(THF): M$_n$=21381 g/mol, M$_w$=54807 g/mol, PD=2, 563

M$_n$=21481 g/mol, M$_w$=80523 g/mol, PD=3.748

In a 100 mL-two-neck flask, equipped with a magnetic stirrer and gas inlet, 25.0 g o-xylene and 0.5 g (2.07 mmol) oxybis-methacrylat are introduced and the mixture is saturated with argon gas for 30 minutes. Subsequently, 3.39 mg (0.020 mmol) N,N-azoisobutyronitrile is added and the reaction mixture is heated to 60° C. Stirring is continued for 48 hours under an argon atmosphere. The polymer solution is precipitated with n-hexane and dried.

GPC(THF): Mn=7825 g/mol, M$_w$=13259 g/mol, PD=1.694

3. Synthesis of polydimethyltetrahydropyran-3,5-dicarboxylate

[214.22]

In a 100 mL-two-neck flask, equipped with a magnetic stirrer and gas inlet, 33.3 g o-Xylene and 1.0 g (4.67 mmol) methyl-4-oxahept-1,6-dien-2,6-dicarboxylate are introduced and the mixture is saturated with argon gas for 30 minutes. Subsequently, 7.66 mg (0.046 mmol) N,N-azoisobutyronitrile is added and the reaction mixture is heated to 60° C. Stirring is continued for 24 hours under an argon atmosphere. The polymer solution is precipitated with n-hexane and the white polymer is dried.

IR: 2999, 2952, 2904, 2850 (ν, —CH3, —CH2), 1730 (ν, —COOR), 1638 (ν, —C=C), 1435, 1391 (δ, —CH3, —CH2), 1155, 1104 (ν, —C—O—C—) cm$^{-1}$.

GPC(THF): M$_n$=4461 g/mol, M$_w$=8478 g/mol, PD=1.900 M$_n$=3749 g/mol, M$_w$=7478 g/mol, PD=1.994

In a 250 mL-two-neck flask, equipped with a magnetic stirrer and gas inlet, 150 g o-Xylene and 5.0 g (23.3 mmol) methyl-4-oxahept-1,6-dien-2,6-dicarboxylate are introduced and the mixture is saturated with argon gas for 30 minutes. Subsequently, 38.3 mg (0.233 mmol) N,N-azoisobutyronitrile is added and the reaction mixture is heated to 60° C. Stirring is continued for 72 hours under an argon atmosphere. The polymer solution is precipitated with n-hexane and the white polymer is dried.

IR: 2996, 2951, 2860 (ν, —CH$_3$, —CH$_2$), 1730 (ν, —COOR), 1634 (ν, —C=C), 1435, 1384 (δ, —CH$_3$, —CH$_2$), 1154, 1105 (ν, —C—O—C—) cm$^{-1}$.

$^1$H-NMR (500 MHz, CDCl3): δ 4.28, 4.18 (br dd, 2H, RCH$_2$OCH$_2$R), 3.64 (br t, RCOOCH$_3$), 2.83 (br d, 2H,

RO₂CCCH₂CCO₂R), 1.78 (br s, R—CH₂—Cyclo) ppm.
¹³C{¹H}-NMR (500 MHz, CDCl₃): δ 173.38 (RCOOCH₃), 71.21 (RCH₂OCH₂R), 52.54 (RCOOCH₃), 44.63 (Cq), 36.42 (RO₂CCCH₂CCO₂R), 20.15 (R—CH₂—Cyclo) ppm.

GPC(DMF):$M_n$=7811 g/mol, $M_w$=24538 g/mol, PD=3.141 Tg~140° C.

4. Synthesis of polytetrahydropyran-3,5-dicarboxylic acid

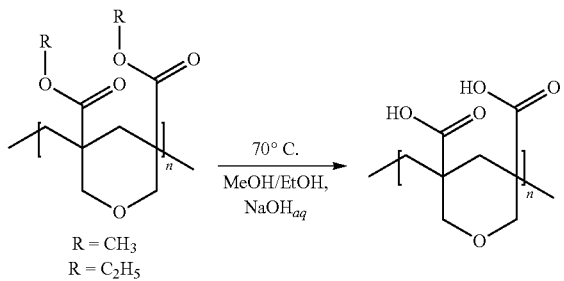

R = CH₃
R = C₂H₅ dissolves in the course of the reaction. Subsequently, the polymer solution is acidified whereby polytetrahydropyran-3,5-dicarboxylic acid is precipitated. The polycarboxylic acid is dried and may be dissolved in an aqueous base.

IR: 2998, 2952, 2863 (ν, —CH₃, —CH₂), 1717 (ν, —COOH), 1437, 1398 (δ, —CH₃, —CH₂), 1157, 1097 (ν, —C—O—C—) cm⁻¹.

¹H-NMR (500 MHz, D₂O): d 4.22, 4.07 (br dd, 2H, RCH₂OCH₂R), 3.50 (br t, RCOOCH₃), 2.98 (br d, 2H, RO₂CCCH₂CCO₂R), 2.38, 2.14 (br dd, 2H, HO₂CCCH₂CCO₂H), 1.37 (br s, R—CH2-Cyclo) ppm.

Preparative Example 2

Synthesis of poly-1,3-diethyl-5,5-dimethylcyclo-hexane-1,3,5,5-tetracarboxylate

1. Synthesis of 2-bromomethylacrylic acid ethyl ester

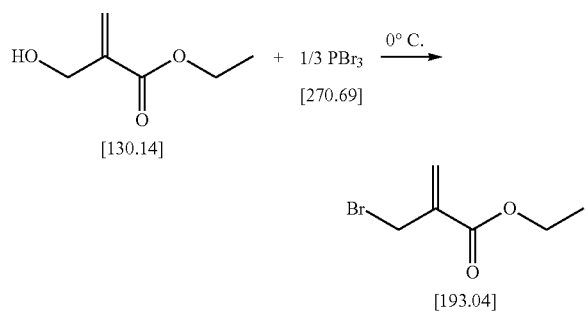

In a 100 ml flask equipped with a magnetic stirrer, a dropping funnel, and a drying tube, 2.3 g (17.7 mmol) 2-hydroxymethacrylic acid ethylester are added to 10 mL absolute diethyl ether. Under ice cooling, 1.92 g (7.08 mmol) phosphorous tribromide in 5 mL absolute diethylether are added dropwise. After 18 hours of stirring at room temperature, any excess phosphorous tribromide is hydrolysed by addition of 10 mL of water under ice cooling. The organic layer is washed twice with saturated NaHCO₃ solution, dried over Na₂SO₄ and stabilized with a small amount of hydrochinon. Diethyl ether is removed under vacuum, IR: 2981, 2933, 2901, 2869 (ν, —CH₃, —CH₂), 1718 (ν, —COOR), 1628 (ν, —C=C), 1463, 1444, 1398 (δ, —CH₃, —CH₂), 1182, 1115 (ν, —C—O—), 957 (ν, RCH=CH₂), 607 (ν, C—Br) cm⁻¹.

GC/MS: m/z 192 (M–H+), 164 (C4H6BrO2+), 146 (C4H4BrO+), 118 (C3H4Br+), 113 (C6H9O2+), 85 (C4H5O2+), 69 (C4H5O+), 57 (C3H5O+), 41 (C3H5+).

¹H-NMR (500 MHz, CDCl₃): d 6.32, 5.93 (s, 2H, RC—CH=CH₂), 4.26 (q, 2H, RCOO—CH₂—CH₃), 4.17 (s, 2H, RC—CH₂—Br), 1.32 (t, 3H, RC—CH₃) ppm.

2. Synthesis of 2,6-diethyl-4,4-dimethyl-hepta-1,6-dien-2,4,4,6-tetracarboxylate

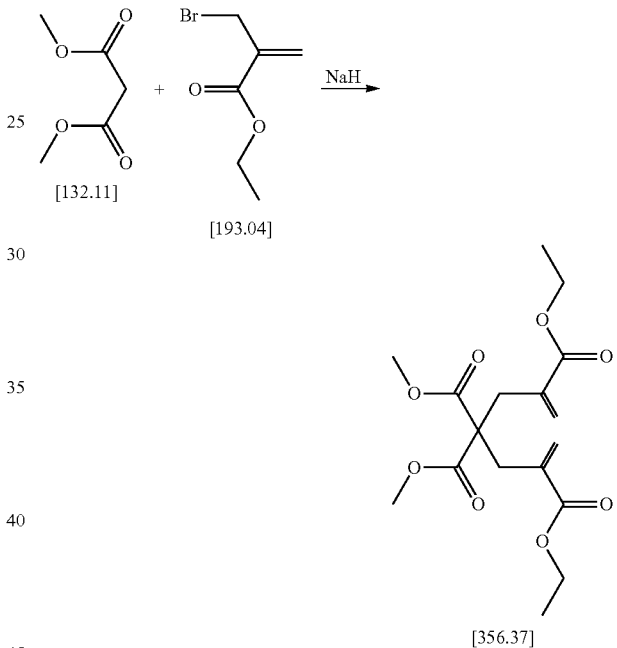

In a 50 mL flask, a cooled suspension of 0.23 g (5.83 mmol) sodium hydride (60% dispersion in mineral oil) in 9 mL acetonitrile p.a. is introduced and 0.34 g (2.59 mmol) malonic acid dimethylester is added. The reaction mixture is stirred 4° C. for 15 minutes, and subsequently as solution of 1.0 g (5.18 mmol) 2-bromomethyl-acrylic acid ethylester in 2 mL acetonitrile p.a. is added. The mixture is stirred at room temperature over a period of two hours. Subsequently, 10 mL of a saturated solution of NaCl are added and extraction is carried out three times with 10 mL diethyl ether, respectively. The combined organic layers are washed with distilled water and an aqueous solution of Na₂CO₃, dried over Na₂SO₄ and stabilized with a small amount of hydrochinone. Diethylether is removed under vacuum.

IR: 2983, 2954, 2904 (ν, —CH₃, —CH₂), 1712 (ν, —COOR), 1629 (ν, —C=C), 1436, 1370 (δ, —CH₃, —CH₂), 1147, 1115 (ν, —C—O—), 954 (ν, RCH=CH₂) cm⁻¹.

GC/MS: m/z 356 (M+), 325 (C16H21O7+), 311 (C15H19O7+), 298 (C14H18O7+), 283 (C14H19O6+), 281 (C14H17O6+), 267 (C13H15O6+), 251 (C13H15O5+), 237

(C12H13O5+), 213 (C10H13O5+), 211 (C11H15O4+), 207 (C11H11O4+), 197 (C10H13O4+), 129 (C6H9O3+), 113 (C6H9O2+), 69 (C4H5O+), 59 (C2H3O2+), 44 (CHO2+).

3. Synthesis of poly-1,3-diethyl-5,5-dimethylcyclo-hexan-1,3,5,5-tetracarboxylate

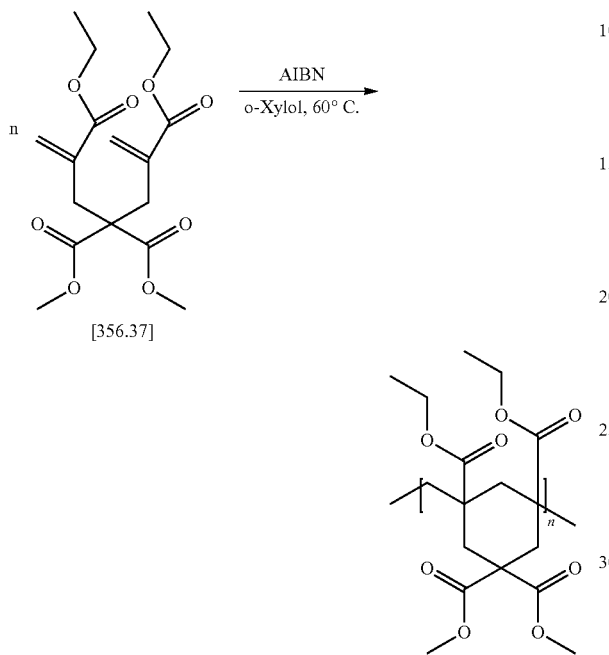

[356.37]

In a 25 mL flask, equipped with a magnetic stirrer and gas inlet, 3.0 g o-xylene and 0.3 g (0.84 mmol) of 2,6-diethyl-4,4-dimethyl-hepta-1,6-dien-2,4,4,6-tetracarboxylate are introduced and the mixture is saturated with argon gas for 30 minutes. Subsequently, 1.38 mg (8.42 μmol) N,N-azoisobutyronitrile is added and the reaction mixture is heated to 60° C. Stirring is continued for 48 hours under an argon atmosphere. The polymer solution is precipitated with n-hexane and the white polymer is dried.

IR: 2977, 2955, 2904 (ν, —CH$_3$, —CH$_2$), 1733 (ν, —COOR), 1434, 1382 (δ, —CH$_3$, —CH$_2$), 1136 (ν, —C—O—) cm$^{-1}$.

GPC(THF): M$_n$=1810 g/mol, M$_w$=2271 g/mol, PD=1.255

Preparative Example 3

Synthesis of a Cyclocopolymer from Divinylether Und Maleic Acid Anhydride (DIVEMA)
1. Synthese Von Divinylether

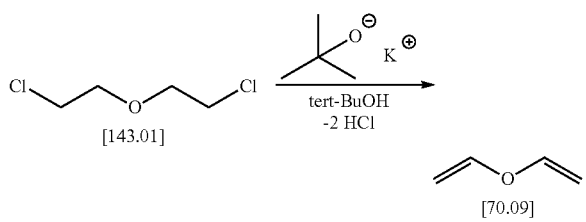

In a 100 mL two-neck flask equipped with a magnetic stirrer and a distillation bridge, 9.39 g (83.7 mmol) potassium tert-butylat in 40 mL wasserfreiem tert-Butanol are introduced and heated to 50° C. By using a septum, 6.0 g (41.9 mmol) 2-chloroethyl ether is added dropwise to the mixture which is heated to 100° C. erhitzt. The reaction mixture becomes turbid. The Die distillation head is cooled with acetone/dry ice.

GC/MS: m/z 70 (M+), 44 (C2H4O2+), 43 (C2H3O+), 31 (CH3O+), 27 (C2H3+).

$^1$H-NMR (200 MHz, CDCl$_3$): δ 6.51-6.41 (dd, 2H, RO—CH=CH$_2$), 4.62-4.54 (dd, 2H, RO—CH=CH$_2$), 4.29-4.25 (dd, 2H, RO—CH=CH$_2$) ppm.

2. Synthesis of a Cyclocopolymer from Divinyl Ether Und Maleic Acid Anhydride (DIVEMA)

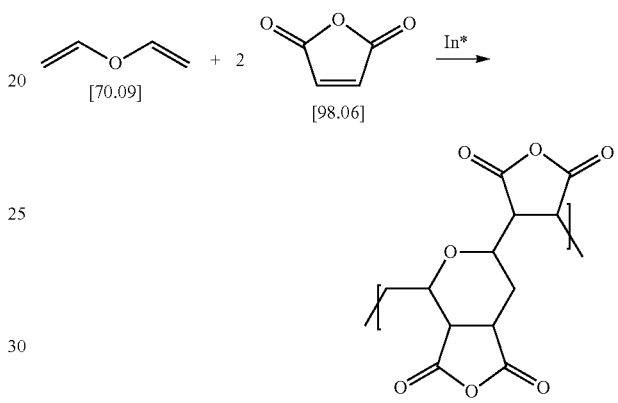

In a 25 mL flask equipped with a magnetic stirrer, 0.5 g (7.13 mmol) divinylether is introduced. Under cooling with ice, an argon saturated solution of 1.40 g (0.014 mol) maleic acid anhydride and 17.3 mg (0.105 mmol) AIBN in 9 mL o-Xylene are added. The mixture is heated for an hour at a temperature of 50° C. und subsequently for three hours at 70° C. The polymer is filtered off, washed with hot o-Xylene gewaschen and dried at 80° C.

IR: 2938 (ν, —CH2), 1850, 1775 (ν, cyclic anhydride), 1625 (ν, —C=C), 1438, 1392 (δ, —CH$_2$), 1223 (ν, cyclic anhydride), 1089 (ν, —C—O—C—) cm$^{-1}$.

$^1$H-NMR (500 MHz, DMSO-d$_6$): δ 4.26 (br, 2H, R$_2$CHOCHR$_2$), 3.90, 3.81 (br, 2H, anhydride-cyclo), 3.20, 2.76 (br, 2H, anhydride-backbone), 1.90 (br, ROCHRCH$_2$R, R—CH$_2$—Cyclo) ppm.

T$_{softening}$~280° C., T$_{decomposition}$~320° C.

DSC(10° C./min): melting area=139.37° C.-220.64° C., 260.26° C.-266.20° C.

DSC(20° C./min): melting area=129.72° C.-212,02° C.

DLS(10 mg/mL H$_2$O): hydrodynamic diameter=3.063 nm

Preparative Example 4

Ring Opening of Anhydride Groups
a) Hydrolytic Ring Opening

Hydrolysis of the anhydride groups was carried out by heating the cyclocopolymer for two hours at 60° C. in distilled water. Subsequently the polymer solution was freeze-dried.

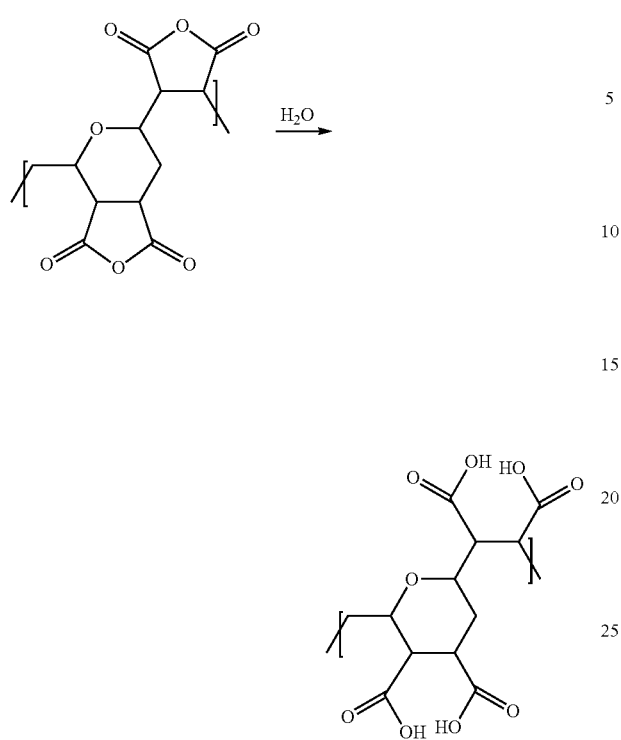

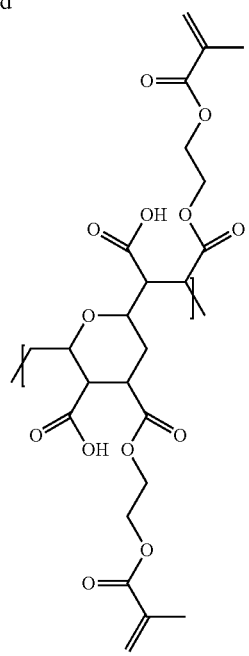

IR: 2926 (ν, —CH$_2$), 1698 (ν, —COOH), 1409 (d, —CH$_2$), 1176, 1082 (ν, —C—O—C—) cm$^{-1}$.

DLS(5 mg/mL H$_2$O): hydrodynamic diameter=4.500 nm

M$_n$=38600 Da, M$_w$=151000 Da, M$_w$/M$_n$=3.90 b) Ring Opening Using Hydroxymethylacrylsäure c) Ring Opening Using HEMA

In order to synthesize functionalized cyclocopolymers, DIVEMA was treated with 2-hydroxyethyl methacrylate at room temperature or 100° C.:

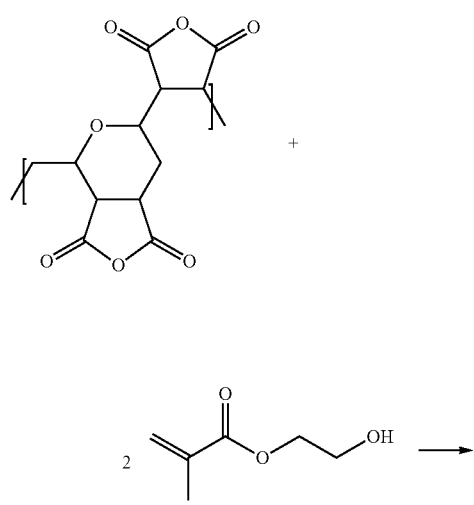

The cyclocopolymer was partially functionalized. The reaction indicates the polymerization of 2-hydroxyethyl methacrylate.

d) Ring Opening Using Cysteamine and Allyl Amine in order to synthesize functionalized cyclocopolymers, DIVEMA was treated with allyl amine and cysteamine. The polymer is soluble in water.

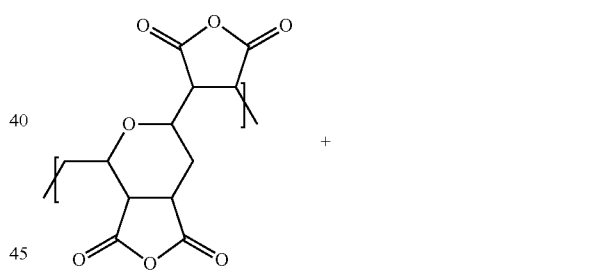

IR: 2929 (ν, —CH$_2$), 1853, 1777 (ν, cyclic anhydride), 1712 (ν, —COOH), 1639 (ν, —C=C), 1639, 1536 (ν, —CO—NH—), 1421, 1356 (d, —CH$_2$), 1207 (v, cyclic anhydride), 1087 (v, —C—O—C—), 991, 923 (d. RCH=CH$_2$) cm$^{-1}$.

$^1$H-NMR (500 MHz, DMSO-de): d 11.64 (br, 4H, RCOOH), 8.01 (br, 2H, —CO—NH—), 5.82 (br, 21H, RCH=CH$_2$), 5.21, 5.08 (br, 4H, RCH=CH$_2$), 3.98 (br, 2H, R$_2$CHOCHR$_2$), 3.81 (br, 4H, —CO—NH—CH$_2$R), 3.74 (br, 2H, anhydride-cyclo), 3.23 (br, 2H, anhydride-backbone), 2.95, 2.70 (br, 2H, RCH-cyclo), 2.70, 2.64 (br, 2H, RCH-backbone), 2.11, 1.91 (br, 2H, ROCHRCH$_2$R), 1.84 (br, 2H, R—CH$_2$—Cyclo) ppm.

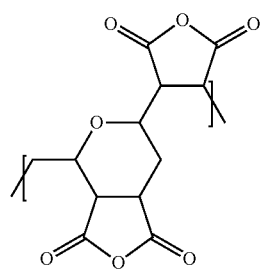

+

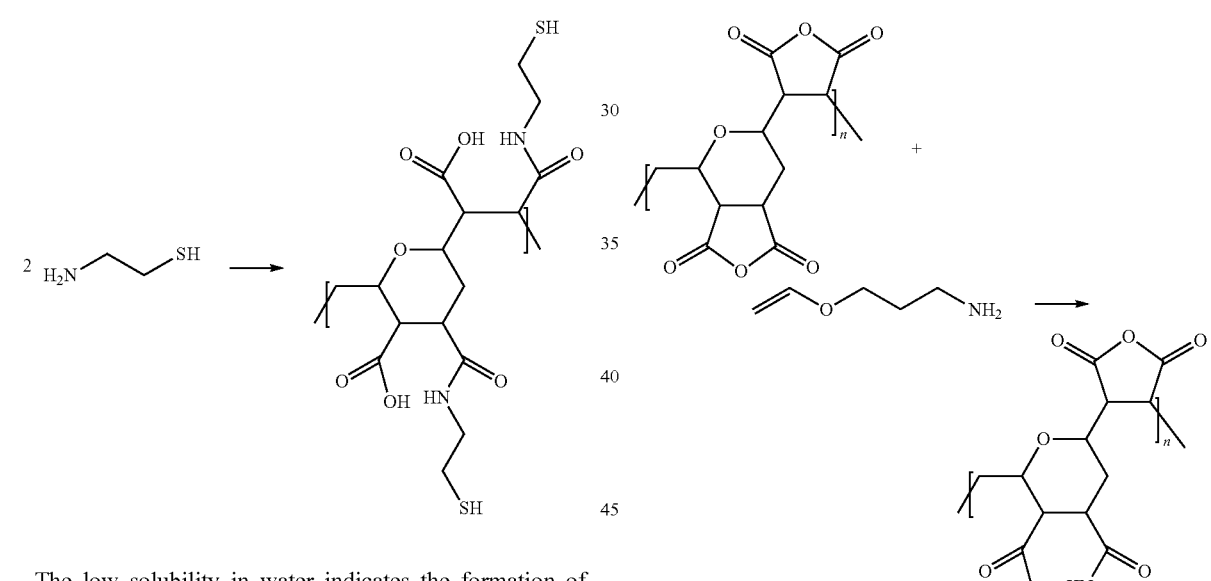

The low solubility in water indicates the formation of disulfide bridges.

IR: 2929 (v, —CH$_2$), 2551 (v, —S$_x$H), 1703 (v, —COOH), 1634, 1536 (v, —CO—NH—), 1381 (d, —CH$_2$), 1192, 1077 (v, —C—O—C—), 753 (v, —S—C—) cm$^{-1}$.

DLS(5 mg/mL H$_2$O): hydrodynamic diameter=13.41 nm

Preparative Example 5

Synthesis of DIVEMA

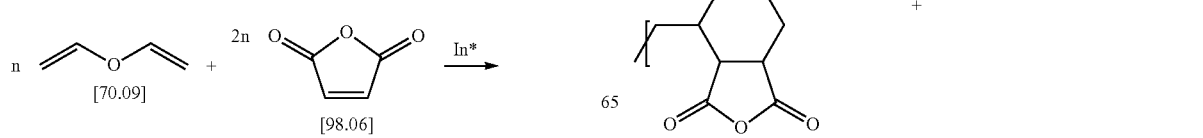

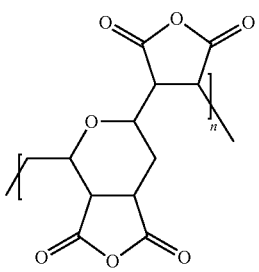

5.44 g (77.6 mmol) divinyl ether are introduced into a 250 mL flask equipped with a magnetic stirrer. A solution saturated with argon gas of 15.2 g (0.155 mol) maleic anhydride (c$_{Monomer}$=1.28 mol/L) und 0.24 g (1.46 mmol, 0.8*10$^{-2}$ mol/L) AIBN in 185 mL Aceton is added. The mixture is heated for 5 hours at 60° C. The polymer solution is precipitated in dry diethyl ether, and the polymer is dried.

GPC(H$_2$O): M$_n$=25700 g/mol, M$_w$=96700 g/mol, PD=3.76

Polymer Analogous Modification.

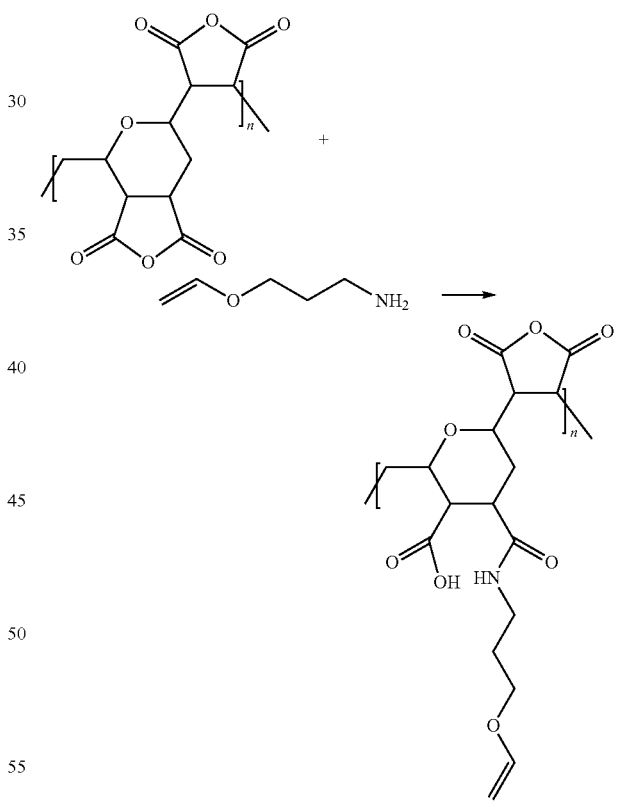

-continued

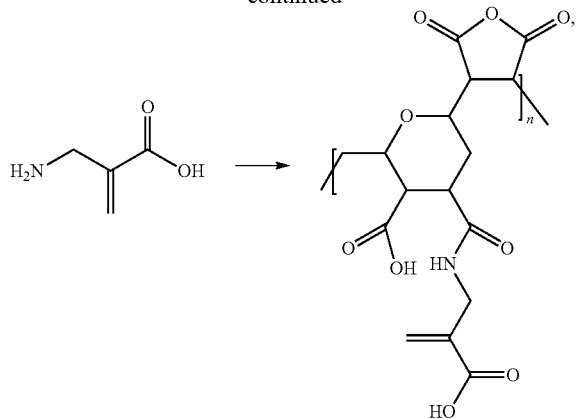

Synthesis of poly(acrylic acid-co-1,3-diethyl-5,5-dimethylcyclohexane-1,3,5,5-tetracarboxylate)

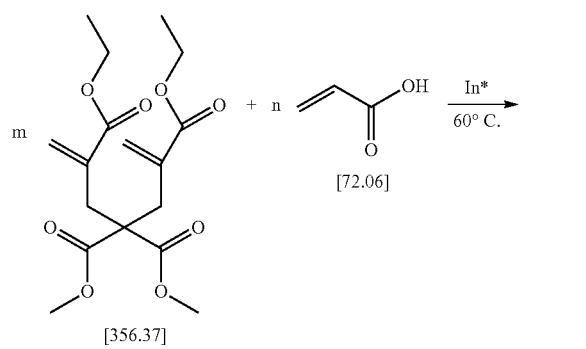

17.6 g DMF, 2.50 g (34.7 mmol) acrylic acid and 1.23 g (3.46 mmol) 2,6-diethyl-4,4-dimethyl-hepta-1,6-dien-2,4,4,6-tetracarboxylate are introduced into a 50 mL-flask equipped with a magnetic stirrer and a gas inlet by which the mixture is saturated with argon gas. Subsequently, 57.0 mg (0.35 mmol) of AIBN are added and the reaction mixture is heated to 60° C. under an argon atmosphere. After 48 hours, the polymer solution is precipitated with distilled acetone. The polymer is separated by centrifuging and the viscous polymer is dissolved in distilled water followed by lyophilization.

IR(DB49-6/1002): 2931 (v, —CH$_3$, —CH$_2$), 1703 (v, —COOH), 1636 (v, —C=C), 1436, 1384 (δ, —CH$_3$, —CH$_2$), 1247, 1161 (v, —C—O—) cm$^{-1}$.

$^1$H-NMR (DB49-6/1002, 500 MHz, DMSO-ds): δ 12.24 (br, RCOOH), 4.14, 3.98 (br, RCOOCH$_2$CH$_3$), 3.60 (br, RCOOCH$_3$), 2.54 (br, RCH$_2$CCOOCH$_3$), 2.19 (br, RCH-COOH), 1.90 (br, RCH$_2$CCOOCH$_2$CH$_3$), 1.73 (br, R—CH$_2$-Cyclo), 1.49 (br, R—CH$_2$—COOH), 1.15 (br, RCOOCH$_2$CH$_3$) ppm.

Application Example 1

1.8 g of the polyacid of example 4 ($M_w$=151000 Da) and 0.2 g tartaric acid were dissolved in 3.00 mL demineralized water. The powder a ground zinc-strontium-calcium-phosphor-aluminum-fluorosilicate glass and the liquid were mixed manually in a ratio of 2:1.

Biaxial flexural strength was determined according to EN ISO 6872 using disk shaped specimens of 20 mm diameter and 1 mm thickness. Compressive strength was determined according ISO 9917-1:2007 using specimens of 4 mm diameter and 6 mm height. All tests were performed on a Zwick Z020 universal testing machine.

The results are shown in the following table:

|  | Application example 1 |
| --- | --- |
| Compressive strength [MPa] | 74 ± 9 |
| Biaxial flexural strength [MPa] | 32 ± 3 |

The invention claimed is:
1. A process for the preparation of dispersed nanoparticles, the process comprising:
condensing a mixture containing one or more compounds of the following formulae (II), (III), or (IV) or a hydrolysis product thereof to form the nanoparticles:

$$X'_m R_{3-m} SiL \quad (II)$$

$$X'_m R_{2-m} SiL'L'' \quad (II)$$

$$X'_m SiL'L''L''' \quad (IV)$$

wherein:
X' represents a hydrolyzable group;
R represents an alkyl, cycloalkyl, cycloalkylalkyl, aralkyl, or aryl group;
L, L', L", and L"', which may be the same or different, are independent from each other and represent an organic group; and
m is 1;
whereby the sum of X', R, L, L', L", and L"' is 4 for each of formula (II), (III), and (IV), and wherein a portion of L, L', L", and L"' is represented by the following formula:

$$\mathrm{-[(CH_2)_oZ]_q(CH_2)_pL''''}$$

wherein:
Z represents an oxygen atom or a sulfur atom;
L"" represents a linear or branched polymer moiety comprising acidic groups and having optionally pendant groups;
o and p, which are independent from each other, may be the same or different and represent an integer of from 1 to 6; and
q represents an integer of from 0 to 12;
wherein a polymer backbone of L"" is obtained by a process comprising:
(i) cyclopolymerizing or cyclocopolymerizing one or more compounds of the following formula (I):

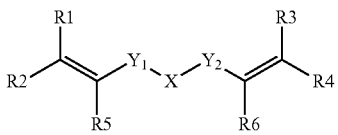

wherein:
X is an oxygen atom, a sulfur atom, an NR⁷ group, or a CR⁸R⁹ group;
Y¹ and Y², which are independent from each other, represent a CR⁸R⁹ group, or a single bond;
R¹ represents an alkyl group, a cycloalkyl group, an aryl group, a JCOOR¹⁰, JCN, JC(O)NHR¹¹, or JC(O)NR¹²R¹³;
R², R³, R⁴, R⁵, R⁶, R⁷, R⁸, and R⁹, which are independent from each other, represent a hydrogen atom, an alkyl group, a cycloalkyl group, an aryl group, a JCOOR¹⁰, JCN, JC(O)NHR¹¹, or JC(O)NR¹²R¹³;
R¹⁰, R¹¹, R¹² and R¹³ which are independent from each other, represent a hydrogen atom, an alkyl group or an aryl group; and
J represents a single bond, an alkylene group, a cycloalkylene group, or an arylene group;
whereby carboxylic acid groups present in R² and R⁵, or R⁴ and R⁶, may form a carboxylic acid anhydride moiety;
optionally (ii) reacting a polymer or copolymer obtained by a process comprising step (i) with a compound for introducing one or more functional groups selected from a polymerizable double bond, a thiol group, or a carboxylic acid group; and
optionally (iii) repeating step (ii) with a polymer or copolymer obtained by a process comprising step (ii) and (iii).

2. The process of claim 1, wherein the cyclocopolymerizing of one or more compounds of formula (I) is with one or more compound selected from the group consisting of acrylic acid, methacrylic acid, itaconic acid, itaconic acid anhydride, maleic acid, maleic anhydride, fumaric acid, methyl acrylate, ethyl acrylate, n-butyl acrylate, t-butyl acrylate, 2-ethylhexyl acrylate, methyl methacrylate, ethyl methacrylate, n-butyl methacrylate, t-butyl methacrylate, 2-ethylhexyl methacrylate, cyclohexyl methacrylate, phenyl acrylate, benzyl acrylate, phenyl methacrylate, benzyl methacrylate, 2-phenylethyl methacrylate, 2-hydroxyethyl acrylate, 2-hydroxyethyl methacrylate, hydroxypropyl acrylate, styrene, 8-methylstyrene, vinylpyridine, N-vinylpyrrolidone, vinyl carbazole, vinyldene halide, and acrylonitrile.

3. The process of claim 1 further comprising reacting a polymer or copolymer obtained by the cyclopolymerizing or cyclocopolymerizing of one or more compounds of formula (I) with a compound for introducing one or more functional groups selected from a polymerizable double bond, a thiol group or a carboxylic acid group, whereby the compound is a bifunctional compound having a functional group reactive with a carboxylic acid anhydride group, carboxylic acid group, or activated carboxylic acid group.

4. The process of claim 1, wherein the polymer backbone comprises acidic groups and/or wherein the pendant groups comprise acidic groups.

5. The process of claim 1, wherein the acidic groups are carboxylic acid groups.

6. The process of claim 1, wherein X is an oxygen atom or a CR⁸R⁹ group, wherein R⁸ and R⁹ are selected from a hydrogen atom, a JCOOR¹⁰, JCN, JC(O)NHR¹¹, and JC(O)NR¹²R¹³.

7. The process of claim 1, wherein R², R³, and R⁴ are hydrogen atoms.

8. The process of claim 1, wherein R⁵ and R⁶, which are independent from each other, represent COOR¹⁰, CN, C(O)NHR¹¹ or C(O)NR¹²R¹³.

9. The process of claim 1, wherein R⁵ and R⁶, which are independent from each other, represent JCOOR¹⁰.

10. The process of claim 1, wherein the linear or branched polymer moiety comprising acidic groups has a molecular weight Mw in the range of more than 1000 to 1,000,000.

11. The process of claim 1, wherein the pendant groups comprise a thiol group.

12. The process of claim 1, wherein the nanoparticles have a size in the range of 1 to 100 nanometers.

13. A process for the preparation of dispersed nanoparticles, the process comprising:
condensing a mixture containing one or more compounds of the following formulae (II), (III), or (IV) or a hydrolysis product thereof to form the nanoparticles:

wherein:
X' represents a hydrolyzable group;
R represents an alkyl, cycloalkyl, cycloalkylalkyl, aralkyl, or aryl group;
L, L', L", and L'", which may be the same or different, are independent from each other and represent an organic group; and
m is 1;
whereby the sum of X', R, L, L', L", and L'" is 4 for each of formula (II), (III), and (IV), and wherein a portion of L, L', L", and L'" is represented by the following formula:

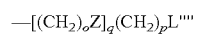

wherein:
Z represents an oxygen atom or a sulfur atom;
L"" represents a linear or branched polymer moiety comprising acidic groups and having optionally pendant groups;
o and p, which are independent from each other, may be the same or different and represent an integer of from 1 to 6; and
q represents an integer of from 0 to 12;
wherein a polymer backbone of L"" is obtained by a process comprising:
(i) cyclocopolymerizing one or more compounds of the following formula (I):

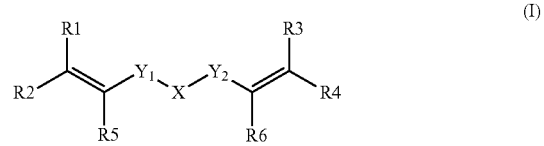

wherein:
X is an oxygen atom, a sulfur atom, an NR⁷ group, or a CR⁸R⁹ group;
Y¹ and Y², which are independent from each other, represent a CR⁸R⁹ group, or a single bond;

R¹, R², R³, R⁴, R⁵, R⁶, R⁷, R⁸, and R⁹, which are independent from each other, represent a hydrogen atom, an alkyl group, a cycloalkyl group, an aryl group, a JCOOR¹⁰, JCN, JC(O)NHR¹¹, or JC(O)NR¹²R¹³;

R¹⁰, R¹¹, R¹² and R¹³ which are independent from each other, represent a hydrogen atom, an alkyl group or an aryl group; and J represents a single bond, an alkylene group, a cycloalkylene group, or an arylene group;

whereby carboxylic acid groups present in R² and R⁵, or R⁴ and R⁶, may form a carboxylic acid anhydride moiety;

wherein the cyclocopolymerizing of one or more compounds of formula (I) is with one or more compound selected from the group consisting of acrylic acid, methacrylic acid, itaconic acid, itaconic acid anhydride, maleic acid, maleic anhydride, fumaric acid, methyl acrylate, ethyl acrylate, n-butyl acrylate, t-butyl acrylate, 2-ethylhexyl acrylate, methyl methacrylate, ethyl methacrylate, n-butyl methacrylate, t-butyl methacrylate, 2-ethylhexyl methacrylate, cyclohexyl methacrylate, phenyl acrylate, benzyl acrylate, phenyl methacrylate, benzyl methacrylate, 2-phenylethyl methacrylate, 2-hydroxyethyl acrylate, 2-hydroxyethyl methacrylate, hydroxypropyl acrylate, styrene, 8-methylstyrene, vinylpyridine, N-vinylpyrrolidone, vinyl carbazole, vinyldene halide, and acrylonitrile;

optionally (ii) reacting a polymer or copolymer obtained by a process comprising step (i) with a compound for introducing one or more functional groups selected from a polymerizable double bond, a thiol group, or a carboxylic acid group; and optionally (iii) repeating step (ii) with a polymer or copolymer obtained by a process comprising step (ii) and (iii).

14. The process of claim 13 further comprising reacting a polymer or copolymer obtained by the cyclocopolymerizing of one or more compounds of formula (I) with a compound for introducing one or more functional groups selected from a polymerizable double bond, a thiol group or a carboxylic acid group, whereby the compound is a bifunctional compound having a functional group reactive with a carboxylic acid anhydride group, carboxylic acid group, or activated carboxylic acid group.

15. The process of claim 13, wherein the polymer backbone comprises acidic groups and/or wherein the pendant groups comprise acidic groups.

16. The process of claim 13, wherein the acidic groups are carboxylic acid groups.

17. The process of claim 13, wherein X is an oxygen atom or a CR⁸R⁹ group, wherein R⁸ and R⁹ are selected from a hydrogen atom, a JCOOR¹⁰, JCN, JC(O)NHR¹¹, and JC(O)NR¹²R¹³.

18. The process of claim 13, wherein R¹, R², R³, and R⁴ are hydrogen atoms.

19. The process of claim 1, wherein R⁵ and R⁶, which are independent from each other, represent COOR¹⁰, CN, C(O)NHR¹¹ or C(O)NR¹²R¹³.

20. The process of claim 13, wherein R⁵ and R⁶, which are independent from each other, represent JCOOR¹⁰.

21. The process of claim 13, wherein the linear or branched polymer moiety comprising acidic groups has a molecular weight Mw in the range of more than 1000 to 1,000,000.

22. The process of claim 13, wherein the pendant groups comprise a thiol group.

23. The process of claim 13, wherein the nanoparticles have a size in the range of 1 to 100 nanometers.

24. A process for the preparation of dispersed nanoparticles, the process comprising:

condensing a mixture containing one or more compounds of the following formulae (II), (III), or (IV) or a hydrolysis product thereof to form the nanoparticles:

X'ₘR₃₋ₘSiL        (II)

X'ₘR₂₋ₘSiL'L"     (II)

X'ₘSiL'L"L'''     (IV)

wherein:

X' represents a hydrolyzable group;

R represents an alkyl, cycloalkyl, cycloalkylalkyl, aralkyl, or aryl group;

L, L', L", and L''', which may be the same or different, are independent from each other and represent an organic group; and m is 1;

whereby the sum of X', R, L, L', L", and L''' is 4 for each of formula (II), (III), and (IV), and wherein a portion of L, L', L", and L''' is represented by the following formula:

—[(CH₂)ₒZ]q(CH₂)ₚL'''' wherein:

Z represents an oxygen atom or a sulfur atom;

L'''' represents a linear or branched polymer moiety comprising acidic groups and having optionally pendant groups;

o and p, which are independent from each other, may be the same or different and represent an integer of from 1 to 6; and q represents an integer of from 0 to 12;

wherein a polymer backbone of L'''' is obtained by a process comprising:

(i) cyclopolymerizing or cyclocopolymerizing one or more compounds of the following formula (I):

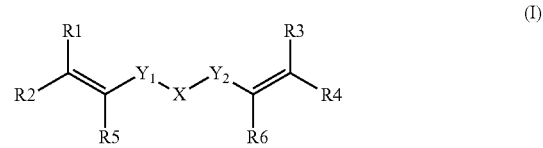

wherein:

X is an oxygen atom, a sulfur atom, an NR⁷ group, or a CR⁸R⁹ group;

Y¹ and Y², which are independent from each other, represent a CR⁸R⁹ group, or a single bond;

R¹, R², R³, R⁴, R⁵, R⁶, R⁷, R⁸, and R⁹, which are independent from each other, represent a hydrogen atom, an alkyl group, a cycloalkyl group, an aryl group, a JCOOR¹⁰, JCN, JC(O)NHR¹¹, or JC(O)NR¹²R¹³;

R¹⁰, R¹¹, R¹² and R¹³ which are independent from each other, represent a hydrogen atom, an alkyl group or an aryl group; and J represents a single bond, an alkylene group, a cycloalkylene group, or an arylene group;

whereby carboxylic acid groups present in R² and R⁵, or R⁴ and R⁶, may form a carboxylic acid anhydride moiety;

(ii) reacting a polymer or copolymer obtained by a process comprising step (i) with a compound for introducing one or more functional groups selected from a polymerizable double bond, a thiol group, and a carboxylic acid group, whereby the compound is a bifunctional compound having a functional group reactive with a carboxylic acid anhydride group, a carboxylic acid group, or an activated carboxylic acid group; and optionally (iii) repeating step (ii) with a polymer or copolymer obtained by a process comprising step (ii) and (iii).

* * * * *